United States Patent
Angeloni Suter et al.

(10) Patent No.: US 11,572,536 B2
(45) Date of Patent: Feb. 7, 2023

(54) WELL INSERTS WITH BRITTLE MEMBRANES

(71) Applicant: SiMPLInext SA, Neuchatel (CH)

(72) Inventors: Silvia Angeloni Suter, Saint-Blaise (CH); Kaspar Suter, Saint-Blaise (CH); Eric Marguet, Saint-Imier (CH); Sylvain Bergerat, Le Russey (FR); Charlotte Voutat, Bole (CH)

(73) Assignee: SIMPLINEXT SA, Bienne (CH)

( * ) Notice: Subject to any disclaimer, the term of this patent is extended or adjusted under 35 U.S.C. 154(b) by 534 days.

(21) Appl. No.: 15/573,708

(22) PCT Filed: May 10, 2016

(86) PCT No.: PCT/EP2016/060468
§ 371 (c)(1),
(2) Date: Nov. 13, 2017

(87) PCT Pub. No.: WO2016/180836
PCT Pub. Date: Nov. 17, 2016

(65) Prior Publication Data
US 2018/0127694 A1 May 10, 2018

(30) Foreign Application Priority Data
May 11, 2015 (WO) .............. PCT/EP2015/060312

(51) Int. Cl.
*C12M 1/12* (2006.01)
*C12M 1/00* (2006.01)
(Continued)

(52) U.S. Cl.
CPC ......... *C12M 1/125* (2013.01); *B29C 45/0001* (2013.01); *B29C 45/0046* (2013.01);
(Continued)

(58) Field of Classification Search
CPC ............ B29C 45/0001; B29C 45/0046; C12M 3/062; C12M 25/04; C12M 1/125; C12M 23/00; C08L 23/00; C08L 2203/02
See application file for complete search history.

(56) References Cited

U.S. PATENT DOCUMENTS 5,026,649 A * 6/1991 Lyman et al. ......... C12M 25/04
422/502
5,139,951 A 8/1992 Butz et al.
(Continued)

FOREIGN PATENT DOCUMENTS

EP   0239697 A2   10/1987
EP   0308129 A1   3/1989
(Continued)

OTHER PUBLICATIONS

International Search Report, dated Nov. 3, 2016, from corresponding PCT application No. PCT/EP2016/060468.
(Continued)

*Primary Examiner* — William H. Beisner
*Assistant Examiner* — Danielle B Henkel
(74) *Attorney, Agent, or Firm* — Nixon & Vanderhye

(57) ABSTRACT

Disclosed is a well insert for cell culture, including: a membrane support having an upper end and a lower end, the upper end being adapted to engage a well of a microplate so as to suspend the well insert therein; and a permeable membrane for supporting a tissue culture, the permeable membrane being attached at the lower end of the membrane support and sealed thereto, the permeable membrane being of brittle material. The membrane support is overmolded or fastened on to the permeable membrane so as be sealed thereto.

17 Claims, 17 Drawing Sheets

(51) Int. Cl.
  *B29C 45/00* (2006.01)
  *C12M 3/06* (2006.01)
  *C08L 23/00* (2006.01)
(52) U.S. Cl.
  CPC ............ *C12M 3/062* (2013.01); *C12M 23/00* (2013.01); *C12M 25/04* (2013.01); *C08L 23/00* (2013.01); *C08L 2203/02* (2013.01)

(56) References Cited

U.S. PATENT DOCUMENTS

| | | | | |
|---|---|---|---|---|
| 6,764,653 B2 * | 7/2004 | Zermani | ............... | B01L 3/5025 |
| | | | | 156/309.9 |
| 2009/0297403 A1 | 12/2009 | Franke et al. | | |
| 2011/0232826 A1 | 9/2011 | Hara et al. | | |

FOREIGN PATENT DOCUMENTS

| | | |
|---|---|---|
| EP | 2061589 A2 | 5/2009 |
| EP | 2735432 A1 | 5/2014 |
| EP | 2548943 B1 | 5/2016 |
| WO | 9301039 A1 | 1/1993 |
| WO | 2013081651 A1 | 6/2013 |

OTHER PUBLICATIONS

"Transwell® Permeable Supports Selection and Use Guide." Corning, 2013, csmedia2.corning.com/LifeSciences/Media/pdf/transwell_guide.pdf.

* cited by examiner

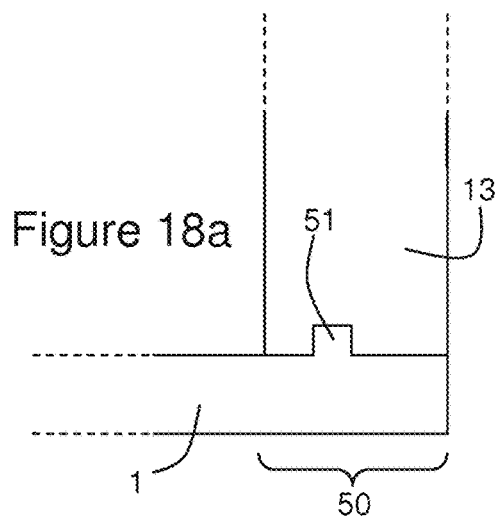
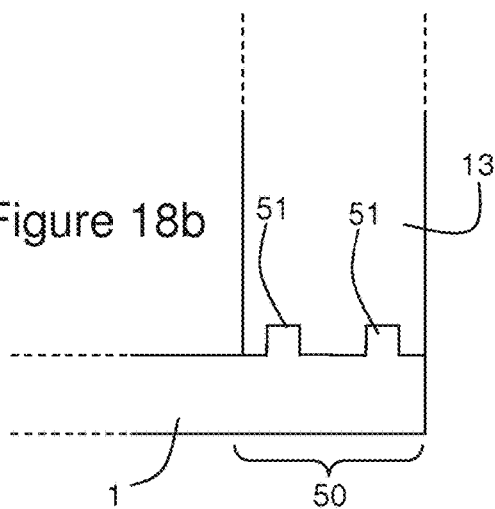
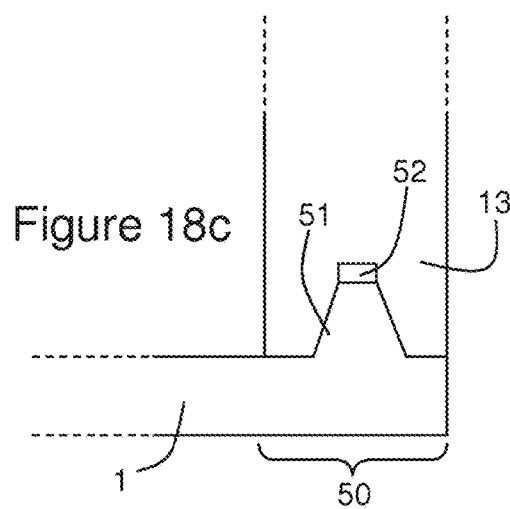
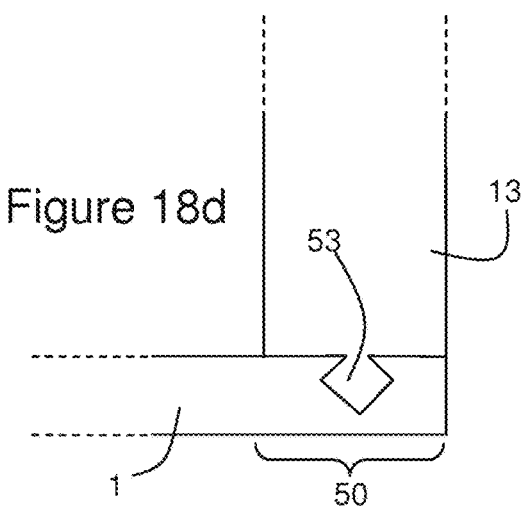
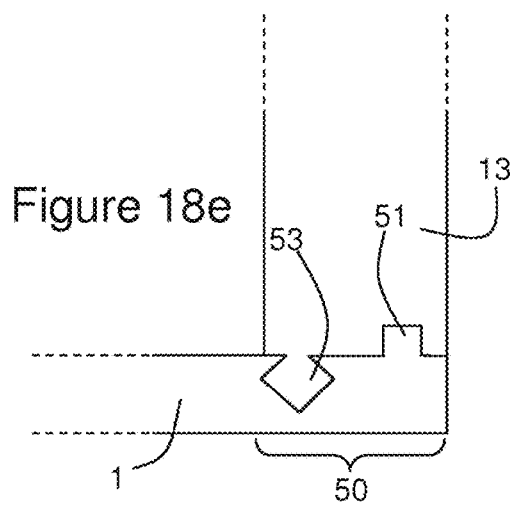
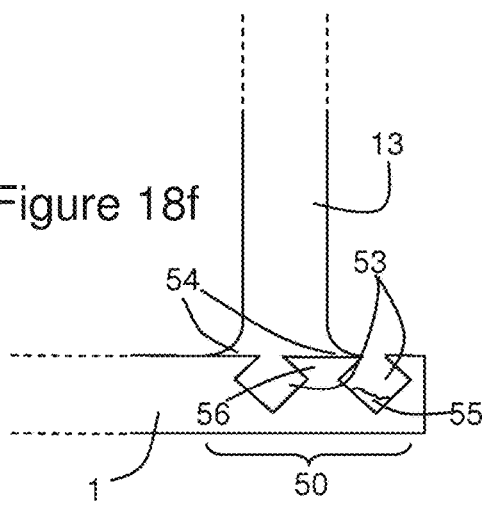

WELL INSERTS WITH BRITTLE MEMBRANES

TECHNICAL FIELD

The present invention relates to the fields of well inserts for use in microplates for cell culture. It relates, more particularly, to well inserts comprising a brittle membrane made of silicon, ceramic (such as silicon nitride), or similar.

STATE OF THE ART

Well inserts for microplates are used for simulating biological barriers, such as lung, skin, the intestines and the blood-brain barrier, for in-vitro testing of pharmaceuticals, toxins and other substances so as to determine their ability to enter into and move around within the human or animal body. In vitro models consist of a single layer or multiple layers of cells that are cultured in the laboratory so as to mimic the properties of biological barriers in the body.

A well insert is used in combination with a microwell plate comprising a number of wells made in plastic. The insert is inserted into a well, which it divides in two, a top (apical) compartment and a bottom (basolateral) compartment which communicate via a porous membrane at the bottom of the insert. Cells are added to the apical side of the well insert and are cultured on the porous membrane. Cells may also be added on the basolateral side and are cultured on that side of the porous membrane, thereby forming complex stacks of layers of different cell types in co-culture, with the membrane taking over the role of a non-vascularized support, thereby becoming an internal structure of the barrier model. Typically, the cells will grow to form a watertight layer sitting on or around the porous membrane that divides the apical from the basolateral compartment, as in the body.

One of the major players in the well insert industry, Corning, produces a variety of such well inserts, which it commercialises under the names "TRANSWELL®", "SNAPWELL™".

The basic TRANSWELL® insert is disclosed in EP 0 239 697, and the more advanced SNAPWELL™ insert, with the membrane supported on a detachable ring, is disclosed in U.S. Pat. No. 5,139,951. In each of these arrangements, the membrane is a porous polymer film, attached to the rigid structure of the insert by heat sealing or solvent bonding.

Such polymer films, while cheap, are relatively thick (of the order of 10 µm), and the pore size ranges typically from 0.4 to 8.0 µm. Furthermore, due to the mechanical and chemical properties of the polyester, polycarbonate and collagen-coated PTFE used the reduction of the film thickness is extremely difficult.

As a result, interest has been shown in using micromachinable materials such as silicon, ceramics such as silicon nitride, alumina and so on for the membranes. Such materials can be micromachined using MEMS and microprocessor-fabrication technologies, and the resulting membranes can have regions which are significantly thinner than polymer membranes, for instance of the order of less than 1 µm thick.

EP 2 548 943 cites membranes fabricated by first depositing a thin layer of ceramic material, such as $Si_3N_4$, on a silicon wafer. Pores are then etched in the $Si_3N_4$ by photolithography followed by a dry etch. The silicon wafer is then etched from the other side to remove the entire thickness of silicon in selected areas, leaving a set of supports for the transparent porous membrane that remain after removal of the silicon. The resulting porous membrane comprises a silicon nitride membrane supported on a silicon frame which gives it suitable mechanical properties. Such a membrane is illustrated in FIG. 1.

Not only are such membranes significantly thinner than the polymer membranes cited above, but the pore sizes, shapes, densities and distributions in such a membrane can be tuned as desired with local high reproducibility and precision of the porous pattern; the membranes are highly transparent in both air and water (polycarbonate membranes are typically translucent) independently of pore size and density, and the membranes are resistant to acids, bases, solvents, high temperatures and e-beam exposure. They are also reusable (reconditionable) after cell culture.

Furthermore, in comparison with polymer membranes they exhibit low intrinsic fluorescence of the membrane, which is important for distinguishing and detecting fluorescence effects of the cells or the substances being tested, chemical pretreatment to enhance cell culture is possible—though not necessary—and they promote good cell growth in general and, in particular, the formation of tight layers of epithelial cells while withstanding common sterilization procedures.

EP 2 548 943 further proposes a cell culture insert for use with such membranes. This insert comprises a clamping and a sealing arrangement intended to permit easy removal of the membrane for reconditioning. However, the clamping arrangement requires a significant number of components, and a significant volume of material in its construction. Insertion and removal of the extremely fragile and brittle membrane is difficult for the technician, increasing the risk of breaking the membranes.

Various other techniques have been proposed in the art for providing cell culture inserts with membranes secured to a culture support or holder.

WO 2013/081651 A1 discloses well inserts wherein the membrane is heat sealed to the holder by partially melting plastic material of the insert's holder to create a solid bond joint to the membrane. Such assembly of the membrane to its holder is theoretically appropriate for attaching membranes of various nature and thickness to a plastic holder. However, it is particularly difficult to control uniform formation of a thin, homogenous joint of the melted material about the periphery of the membrane. Additionally, the amount of energy required to melt the support material may in some instances affect the physical integrity of the membrane depending on the material and thickness thereof.

EP 0 308 129 A1 further discloses a well insert comprising an alumina or metal oxide membrane being overmoulded in the bottom of a substantially conical plastic support. Such technique is however not applicable as such with very thin fragile brittle membranes of silicon nitride of only a few micrometres or tenths of micrometres.

An object of the present invention is thus to overcome the disadvantages of known types of well insert identified above, and thus to facilitate use of modern, ultrathin, brittle membranes in an economic manner.

DISCLOSURE OF THE INVENTION

More precisely, the invention proposes three main embodiments which provide solutions to the above-mentioned problems of the prior art by combining microfabricated component(s) with a polymer based packaging design.

A first embodiment relates to a well insert for cell culture, comprising a membrane support having an upper end and a lower end, said upper end being adapted to engage a well of a microplate so as to suspend the well insert therein. The membrane support may be constructed of a single piece, or may be a multi-piece arrangement such as in the SNAP-WELL™ mentioned above, which comprises a separate hanger.

The well insert further comprises a permeable membrane for supporting a tissue culture, the permeable membrane being attached at said lower end of the membrane support and sealed thereto, the permeable membrane being of brittle material, i.e. a material which does not exhibit a plastic deformation regime and thus will fail before it deforms plastically, and preferably a membrane having a thickness of less than 10 µm, still preferably in the range of 0.1 to 10 µm. Examples of such materials are silicon, silicon nitride, various ceramics, various glasses, and various glass-ceramics. To be considered as a "permeable membrane", at least a portion of the membrane must be permeable—it is not necessary that the whole area of the membrane be permeable.

According to the invention, the membrane support is made of a polymer exhibiting a linear shrinkage of 1-4% in the radial direction of the permeable membrane, which is overmoulded on to the permeable membrane so as be sealed thereto. Hence, a brittle membrane can be integrated into a well insert, removing any need for lab technicians to assemble the fragile membranes to the well inserts, making their use simpler. It should be noted that the fact that overmoulding has been used is directly visible in the finished well insert.

Advantageously, the membrane support is directly sealed to the permeable membrane, obviating any need for separate sealing pieces. Essentially, the material of the well insert can, due to the use of overmoulding, contact the membrane sufficiently intimately so as to provide a sealed joint.

Advantageously, the membrane support comprises at least one flange in contact with a first side of the membrane, and at least one opposing flange in contact with a second side of the membrane, said second side being opposite said first side. The membrane is thus "pinched" and held in sandwich by the material of the membrane support. This improves sealing between the membrane and the membrane support.

The at least one opposing flange may be continuous or may be a plurality of opposing flanges separated by notches, and the said at least one flange may be continuous or is formed as a plurality of individual flanges.

The membrane may be recessed with respect to an end face of the membrane support, thereby avoiding contact between the membrane and a surface upon which the well insert is placed. Alternatively, a face, i.e. the lower face, of the membrane may be flush with respect to an end face of the membrane support.

Advantageously, the membrane support is of polyolefin material or any other polymer with a suitable shrinkage during moulding. These materials provide good sealing without risking damaging the membrane, and provides the requisite biocompatibility.

This first embodiment also relates to a method of manufacturing a well insert as defined above, comprising the following steps:
  providing a permeable membrane of brittle material;
  providing a source of molten polymer at a temperature T;
  providing an injection moulding tool comprising a male part and a female part;
  positioning the permeable membrane in the injection moulding tool;
  closing the injection moulding tool so as to form a cavity in which the permeable membrane is situated, the cavity being shaped so as to conform to the shape of the well insert before solidification of the molten polymer, i.e. of dimensions calculated such that, when the polymer has cooled, the desired shape of the well insert is attained;
  injecting a quantity of molten polymer into the cavity, the molten polymer flowing around the periphery of the permeable membrane and intimately contacting the periphery of the permeable membrane;
  hardening the molten polymer such that it applies a radial force around the periphery of the permeable membrane;
  opening the moulding tool;
  removing the well insert from the moulding tool.

This method provides an economic method for producing well inserts comprising a brittle membrane, which obviate the need for a technician to handle the membranes directly.

Advantageously, the material of the molten polymer, the shape of the cavity, and the initial temperature T of the molten polymer are chosen such that, upon cooling to room temperature and solidifying, the polymer exhibits a linear shrinkage of 1-4%, preferably 1.5-2.5% in the radial direction of the permeable membrane. This provides good sealing, while reducing the risk of breaking the membrane during moulding or during handling of the well insert. The skilled person knows how to perform the required calculations for a given size and shape of well insert.

Advantageously, the permeable membrane is positioned in the injection moulding tool by means of a vacuum.

Advantageously, the male part of the injection moulding tool comprises a seat shaped to receive a membrane. The male part of the injection moulding tool may further comprise at least three abutments distributed around said seat, said abutments being adapted to position the permeable membrane radially. Good support of the membrane in the mould is thus obtained, reducing risk of applying undesired bending or torsion to the membrane during injection moulding and thereby reducing the risk of breaking the membrane.

Advantageously, the abutments have a height of at least 0.75 mm and no more than 20% of the thickness of the permeable membrane. The abutments are thus sufficiently large to tolerate a certain degree of wear, and yet are not so large as to cause weak spots in the contact between the membrane and the membrane support. Such weak spots may be inadequately sealed, and hence their avoidance is desirable.

The male part of the injection moulding tool may also further comprise at least one abutment shaped so as to fit into a hollow surface feature of the membrane. This provides another way of supporting and positioning the membrane in the mould which eliminates the need for abutments situated on the outside of the membrane.

The abutments, whatever their configuration, may be provided on a removable insert. They can thus be easily replaced if they are worn out without having to replace the entire mould.

Advantageously, the female part of the injection moulding tool comprises a vent to permit escape of air during injection of the polymer material, the vent being axial with respect to the membrane. Since this vent is axial with respect to the membrane, it allows air inside the mould to be displaced evenly, allowing the polymer melt to flow evenly through the mould and around the membrane, improving the quality of the moulding and preventing uneven application of force by the melt to the membrane.

Advantageously, when the injection moulding tool is closed, a play of 2-4 µm is present between a flat surface of the permeable membrane and a surface of the female part of the injection moulding tool which faces said flat surface. This play is sufficient to permit air to escape, however is not so great as to permit the membrane to tilt so much that the polymer melt may flow under one side and apply excessive bending or twisting forces thereto that could cause the membrane to break A second embodiment of the invention relates to a well insert for cell culture, comprising a membrane support having an upper end and a lower end, said upper end being adapted to engage a well of a microplate so as to suspend the well insert therein. As for the first embodiment, membrane support may be constructed of a single piece, or may be a multi-piece arrangement such as in the SNAPWELL™ mentioned above, which comprises a separate hanger.

The well insert further comprises a permeable membrane for supporting a tissue culture, the permeable membrane being attached at said lower end of the membrane support and sealed thereto, the permeable membrane being of brittle material, i.e. a material which does not exhibit a plastic deformation regime, and comprising surface features arranged in a surface thereof. Examples of such materials are silicon, silicon nitride, various ceramics, various glasses, and various glass-ceramics. To be considered as a "permeable membrane", at least a portion of the membrane must be permeable—it is not necessary that the whole area of the membrane be permeable.

According to the invention, the membrane support is fastened to the permeable membrane in the surface features thereof.

In the context of the present invention, the term "fastened" should be understood under its standard meaning, i.e. attached firmly and securely, especially by pinning, tying or nailing. The fastening of the membrane support to the membrane is achieved according to the invention by insertion and retention of the membrane support into said surface features arranged in the membrane. Said insertion of the membrane support is advantageously achieved by melting the membrane support material and/or a surface layer of the membrane at their interface, e.g. by laser, infrared heating, thermal contact with a hot plate, or application of ultrasonic energy, so as to allow molten material to wet said interface and to flow into the surface features, which are arranged in the membrane surface at the periphery thereof and by subsequent cooling of the molten material, either at ambient temperature or by external cooling. Upon cooling the molten material actually bonds the material support and membrane uniformly and homogeneously about the membrane periphery and further mechanically fastens said support through formation of hardened protrusions forming pillars or nails in the microstructures. Such fastening improve the strength and sealing of the connection between the membrane support and the membrane An alternative solution to overmoulding is thus proposed for a directly-integrated well insert, which comprises the same advantages as given above in relation to the first embodiment.

Advantageously, the membrane comprises a joining zone on a planar surface thereof, said planar surface facing said membrane support and comprising said surface features into and/or around which the material of the membrane support extends.

The surface features may comprise at least one of protrusions (such as ridges and lugs), recesses (such as grooves and notches), and undercut portions. Particularly interesting are grooves provided with undercuts, which may be produced by anisotropic etching along the crystal planes of the material of the membrane. Such surface features may be combined, e.g. by using at least one protrusion and at least one recess, said at least one recess ideally being undercut. Each of said protrusion and said recess may extend around the periphery of the membrane, optimizing sealing.

Advantageously, said protrusion is situated towards the periphery of the membrane.

Advantageously, the surface features comprise at least one recess formed as a first groove, said first groove extending around the membrane on a planar surface thereof, said surface features further comprising a plurality of further grooves arranged perpendicular to said first groove. This arrangement provides excellent fastening, actually anchoring and sealing.

This second embodiment further relates to a method of manufacturing a well insert as defined above, comprising the steps of:
 providing a permeable membrane of brittle material comprising surface features in a surface thereof;
 providing a membrane support made of plastics material;
 placing said membrane support in contact with a planar surface of said membrane;
 melting said plastics material in contact with said membrane so as to allow the molten material to flow into the surface features, and
 allowing the molten material to cool so as to fasten said membrane support to said membrane.

This method thus results in the production of the well insert as above, which has the noted advantages.

Advantageously, said step of melting said plastics material comprises heating by means of at least one of:
 laser energy, either through the membrane or from the side;
 ultrasonic energy;
 thermal contact with a hotplate
 infrared radiation.

Advantageously, the surface features may comprise at least one recess or groove, and said step of melting said plastics material may comprise causing said plastics material to flow into said recess or groove. This provides good sealing and good anchoring upon cooling of the molten plastics material.

The third embodiment of the invention relates to a well insert for cell culture, comprising: a membrane support comprising an hanger having an upper end and a lower end, said upper end being adapted to engage a well of a microplate so as to suspend the well insert therein, and a permeable membrane for supporting a tissue culture, the permeable membrane being in arranged at said lower end of the hanger and sealed thereto, the permeable membrane being of brittle material. This membrane is as defined above in reference to the first and second embodiments.

According to the invention, the membrane support comprises a seal arranged at said lower end of said hanger, which may be integral with the hanger or may be a separate piece, and the membrane support further comprises an end piece releasably clipped to said hanger so as to support said membrane between said end piece and said hanger in contact with said seal. In other words, the membrane support comprises two pieces. The end piece is arranged so as to cause said membrane to compress said seal upon clipping of the end piece to said hanger.

Thus, a simpler, more compact arrangement to that described in EP 2 548 943 is provided. This arrangement requires less material to produce, and permits easier handling of the membrane since it no longer needs to be placed at the bottom of a bore.

The end piece is furthermore thus situated outside of said hanger.

Advantageously, the end piece comprises a plurality of arms extending towards said upper end and comprising first clipping elements each interfacing with a corresponding second complementary clipping elements provided on said hanger. Such an arrangement facilitates "clipping" the end piece onto the hanger so as to compress the seal. These first clipping elements may be hooks, and/or the second clipping elements may be openings provided in said hanger. Alternative arrangements are also possible.

BRIEF DESCRIPTION OF THE DRAWINGS

Further details of the invention will appear more clearly upon reading the following description, in reference to the annexed drawings, which show:

FIG. 17b—a cutaway view of the membrane of 17a joined to a membrane support;

FIG. 18a-j—schematic views of various arrangements of structural features for improving the attachment between the membrane and the membrane support.

EMBODIMENTS OF THE INVENTION

Generalities

In the figures, the same reference signs have been used throughout to indicate the same or equivalent parts.

Figure 1:
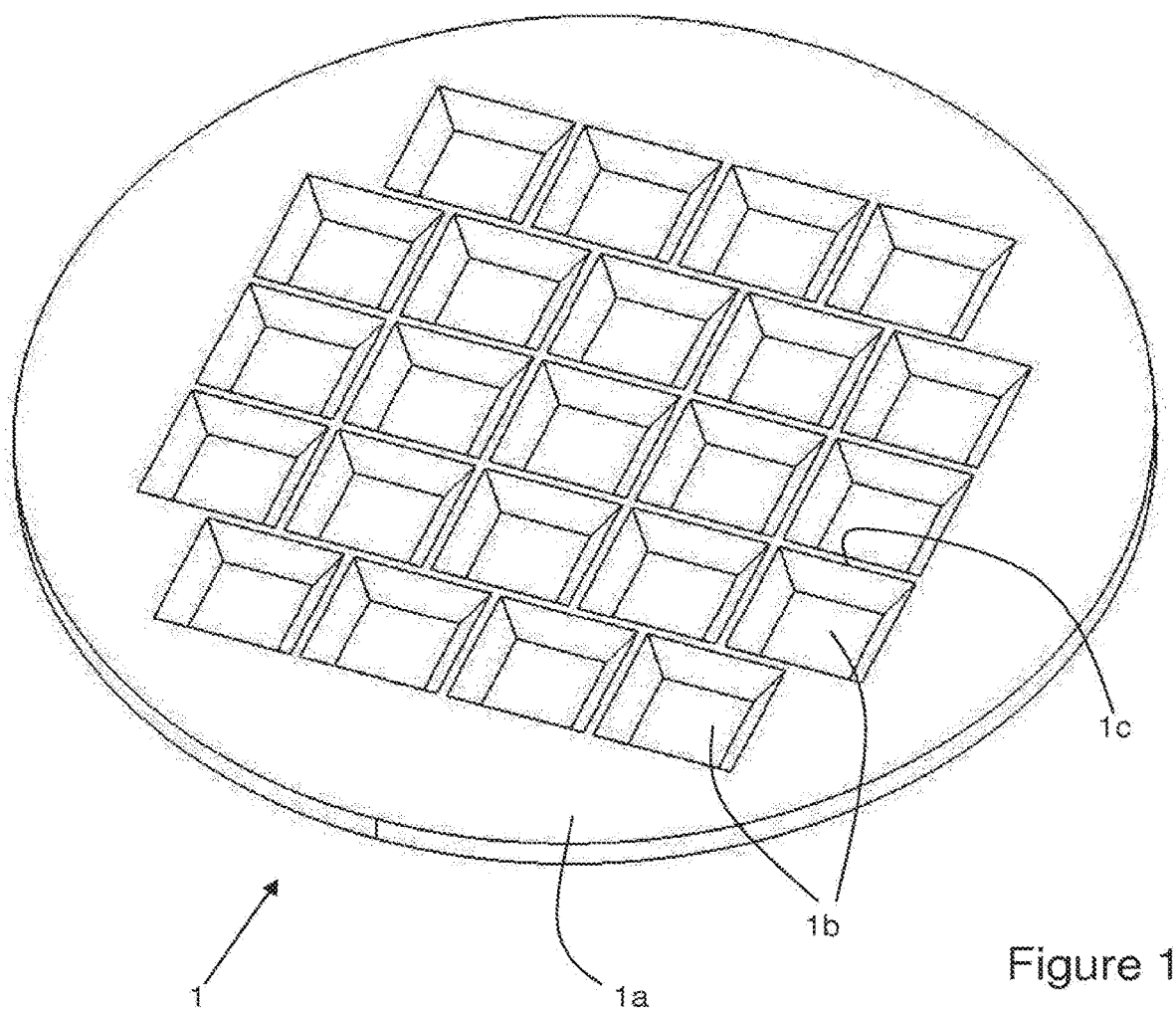
FIG. 1—a typical permeable membrane made of a brittle material.

FIG. 1 illustrates an example of a membrane 1 typical for use with well inserts according to the invention. Although only a portion of membrane 1 is actually porous, for ease of reading the terms "membrane" and "permeable membrane" are used interchangeably to apply to the entire piece 1, which is appropriate since it comprises porous sections and is thus at least partially porous. Membrane 1 is typically made of silicon, silicon nitride, silica or other brittle material (e.g. ceramics, glasses, glass-ceramics) without a plastic deformation regime, i.e. will break without previously being permanently deformed. Membrane 1 comprises a thicker portion section 1a around the periphery of the membrane 1, and a plurality of thinner portions 1b, which are structured with pores so as to be permeable to e.g. ions, water, cell culture media, biological molecules and so on as according to requirements. Thinner portions may be structured by any convenient process such as machining, grinding, laser etching, wet etching, reactive ion etching, anisotropic etching of microstructures, and so on, to create a desired porosity. Between individual thinner portions is a grid structure of thicker material 1c, which define recesses at the bottom of which are situated the thinner portions 1b. Frame section 1c provides structural integrity to the membrane 1. Thicker portion 1a and the grid structure 1c are typically of the order of 200-1000 µm thick, whereas the thinner portions 1b are typically of the order of 100 nm to 10 µm thick, this latter thickness normally being chosen in function of the desired pore diameters, and are as a result very fragile. Indeed, the overall membrane is exceedingly fragile and thus difficult to handle in both a manufacturing setting and in the laboratory. The microfabrication techniques used to create the membranes and pores may be also used to further functionalize either side or both sides of the membrane, such as depositing another thin layer of metal or dielectric to reduce pore diameter or exploit non conventional effect such as light surface interaction (plasmonics), or by adding electrodes, thermocouples, local heaters or coolers, sensors or sensor arrays for temperature, pressure, photodetectors, actuators, MEMS, microfluidic systems, etc., local processing power to condition and read/write out data generated by any electronic components formed thereupon. Different types of functionalization can be identified e.g. by colour coding the well insert 10.

It is upon the surface of the membrane, and particularly in contact with the thinner portions 1b, that cells will be cultured.

For ease of reading, the face of the membrane 1 intended to face the outside of the well insert 10 is considered to be the "lower" face, and the face of the membrane 1 intended to face the inside of the well insert 10 is considered to be the "upper" face. Likewise, the end of the well insert 10 closed by the membrane 1 is considered to be the "lower" end, and the open end of the well insert 10 is considered to be the "upper" end.

Embodiment 1: Overmoulding

Figure 2:
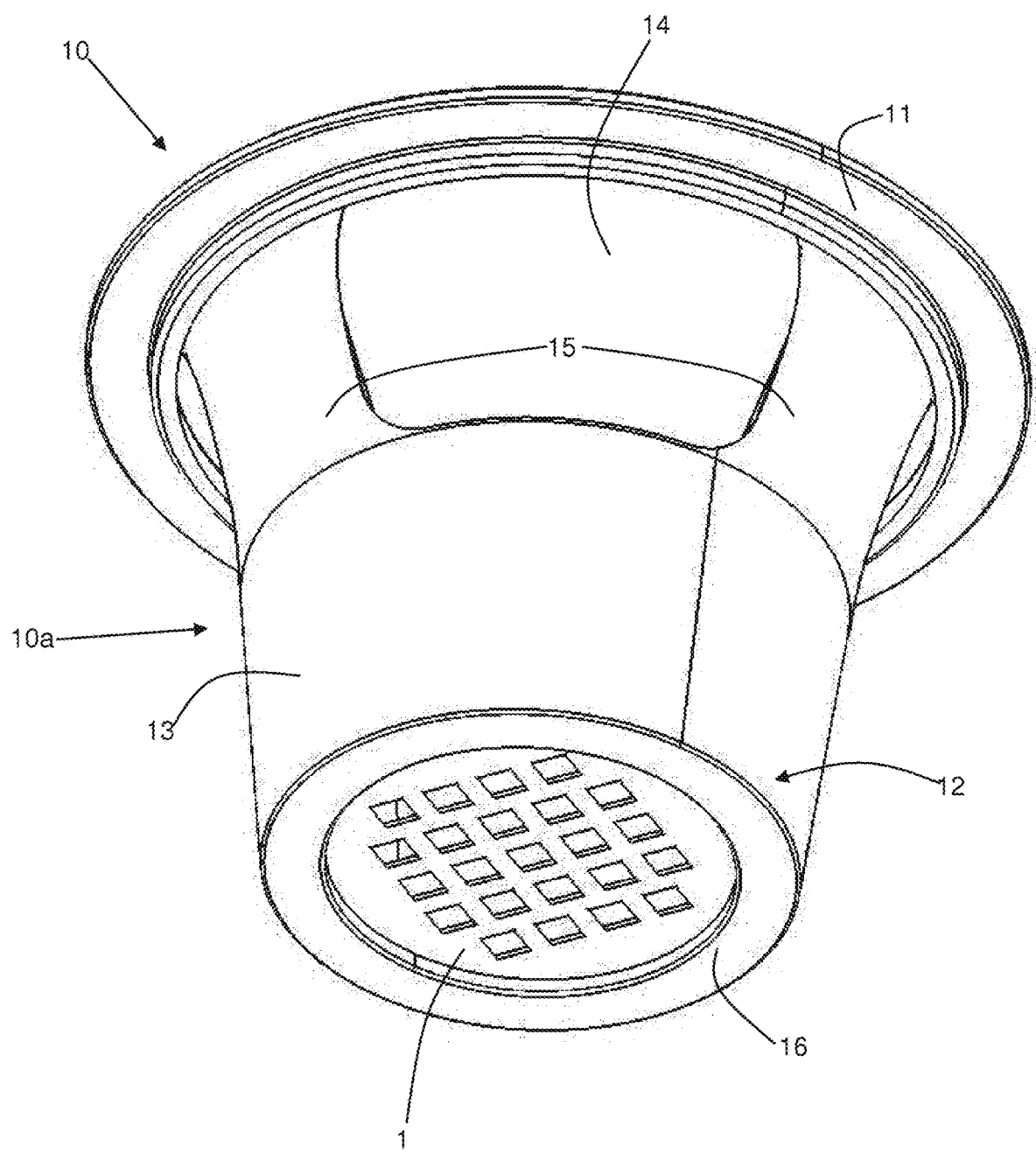
FIG. 2—a perspective view from underneath a well insert according to a first embodiment of the invention.

FIG. 2 illustrates a perspective view from below of a well insert 10 according to a first embodiment of the invention.

Globally, the structure of the well insert 10 is similar to the TRANSWELL® insert mentioned in the introduction, and comprises a membrane support 10a supporting membrane 1. As such, at a first, open end it comprises a flange 11 sized to interface with a well of a microplate (not illustrated) so as to suspend the well insert 10 therein. At a second end 12, the well insert 10 supports the membrane 1 as will be described below. Adjacent to the second end 12 is a first intermediate section comprising an impermeable sidewall 13 which, together with the membrane 1, form a vessel constituting an apical cavity when suspended in the well of a microplate. Joining the impermeable wall to the flange 11 is a second intermediate section, comprising a plurality of openings 14 divided by connecting elements 15. These openings permit access to the basolateral compartment of the well of the microplate when in use.

Membrane support 10*a* is constructed of plastics material, as is generally known. For reasons that will be given below, polyolefin material is particularly suitable, however other plastics are certainly possible.

Figure 3:
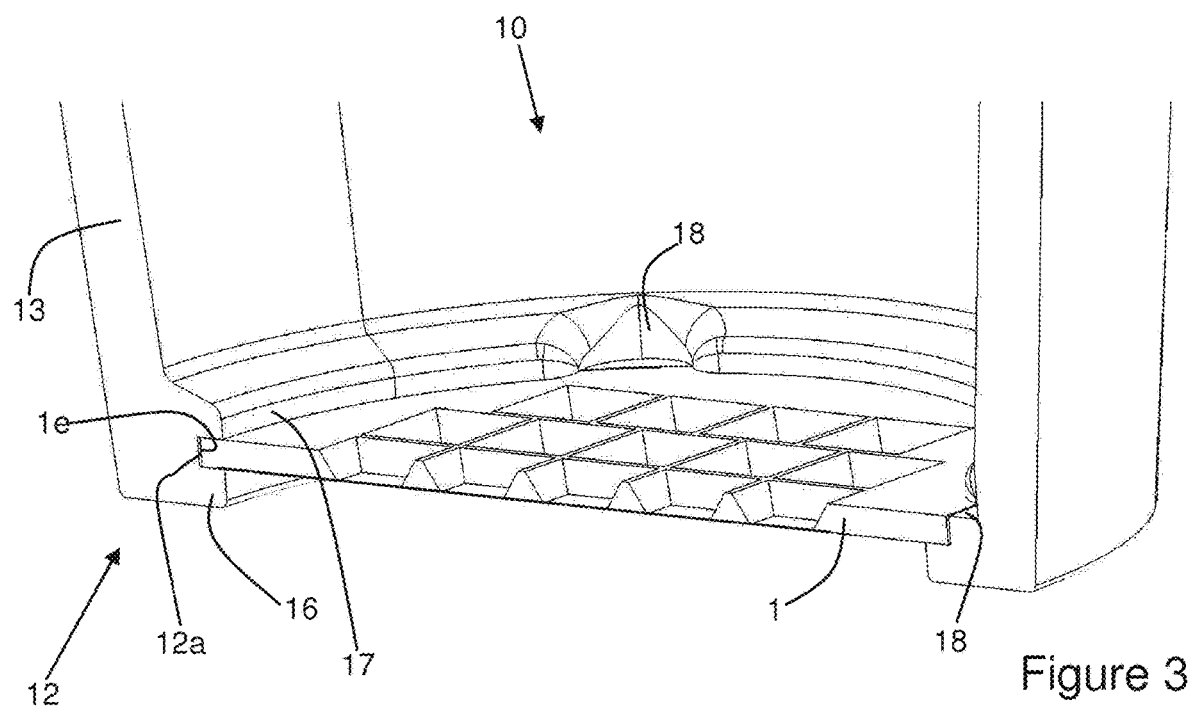
FIG. 3—a cutaway view of the lower end of the well insert of FIG. 2.

FIG. 3 illustrates a perspective sectional view of the well insert of FIG. 2, focusing on the second, lower, end 12.

The membrane 1 is integrally moulded into the structure of the second end 12 of the well insert 10. Up to now, this has not been successfully achieved. The types of materials mentioned above for the membrane 1 are exceedingly fragile in bending, torsion and shear. They have excellent mechanical strength in compression, however in view of the forces required to ensure hermetic sealing directly between the material of the membrane support 10*a* and the membrane 1, if there is any asymmetry in the distribution of forces, torsion or bending of the membrane 1 will occur. Indeed, early injection moulding experiments resulted in the complete destruction of the membrane 1, it having been reduced to powder during the injection moulding process. It is largely for this reason that it was not an obvious choice to use injection moulding, and indeed significant effort was required to successfully achieve overmoulding.

As can be seen in FIG. 3, in the finished well insert 10, membrane 1 is supported from underneath (i.e. on the exterior side of the well insert 10) by an annular flange 16, extending around the periphery of the membrane 1 and towards the centre of the membrane 1 for a certain distance. On the opposite side of the membrane 1, i.e. on the upper side (on the inside of the well insert), the membrane 1 is supported by a plurality of opposing, arcuate, flanges 17 separated by notches 18. In the example illustrated, three opposing flanges 17 are separated by three notches 18 distributed at equal angular intervals around the membrane 1. Other numbers are likewise possible, however three appears to be optimal. The peripheral sidewall of the membrane 1 is also in contact with a corresponding cylindrical wall 12*a* of lower end 12 of the membrane support 10*a*. The significance of these notches will become more apparent below in the discussion of the corresponding injection moulding tool. It should be noted that at each of the notches 18, material of the membrane support 10*a* is not present on the upper side of membrane 1.

Due to the presence of annular flange 16, the membrane 1 is recessed from the lower surface of the membrane support 10*a* and thus cannot not come into contact with a surface on which the well insert 10 is placed.

Experiments have shown that the choice of material, particularly but not exclusively polyolefin material, the temperature of the melt, the dimensions of the flanges 16, 17 and the thickness of the material adjacent to the cylindrical wall 1*e* of the membrane 1 are chosen so as to exhibit, in the theoretical absence of the membrane 1, a 1-4%, better a 1.5-2.5%, even better a 2% linear shrinkage. In the case of polyolefin, PMMA, or polycarbonate, a melt temperature of approximately 250° C. achieves this shrinkage. In the case of PEEK, approximately 420° C. is more appropriate. Other polymer materials and other melt temperatures are of course possible. As a result, a force is applied radially on the cylindrical wall 1*e* of the membrane 1, as well as an axial clamping force applied between flanges 16 and 17, is sufficient to hermetically seal the membrane 1 to the membrane support 10*a*, while the forces are insufficient to damage the membrane 1 either during moulding or in use.

Figure 4:
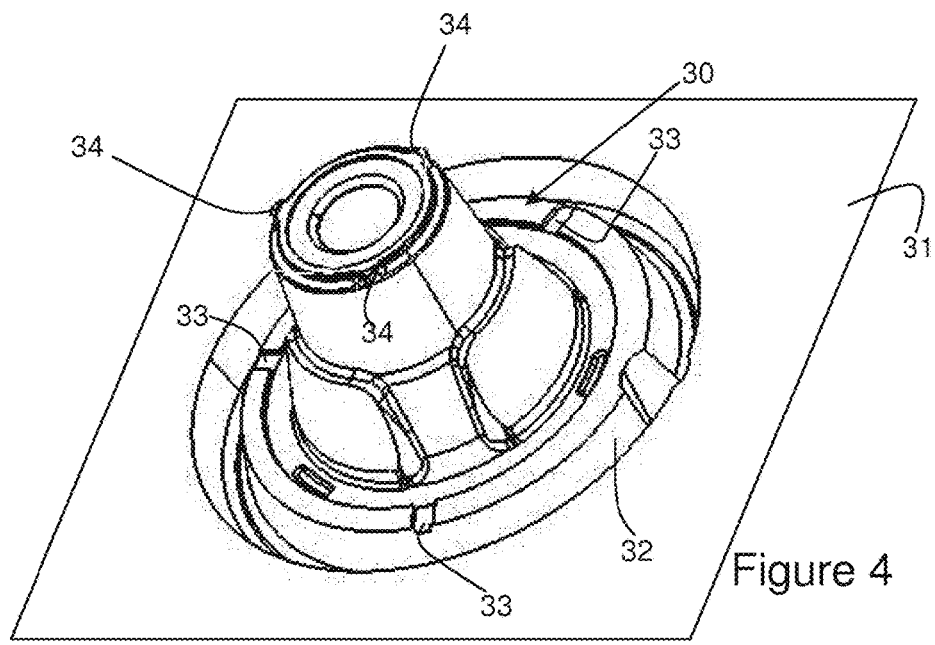
FIGS. 4 and 5—perspective views of a male part of an injection moulding tool for producing a well insert as shown in FIG. 2.
Figure 5:
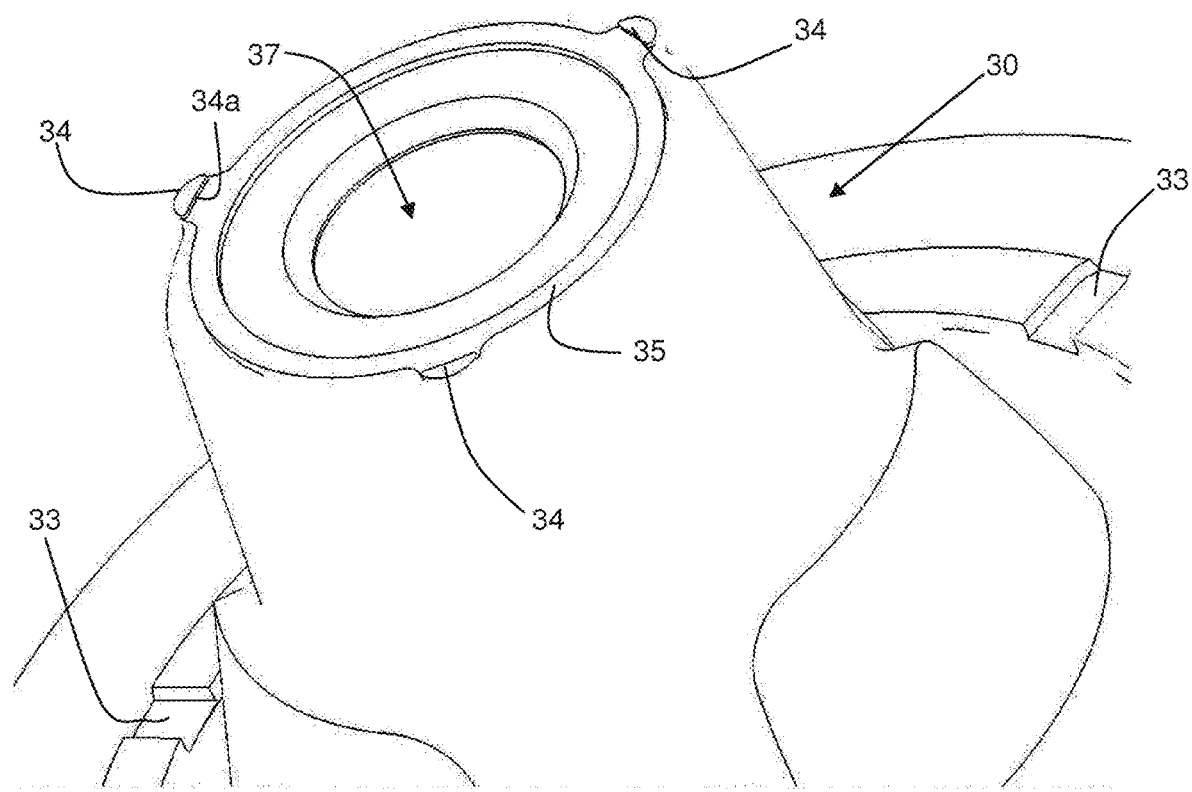
Figure 6:
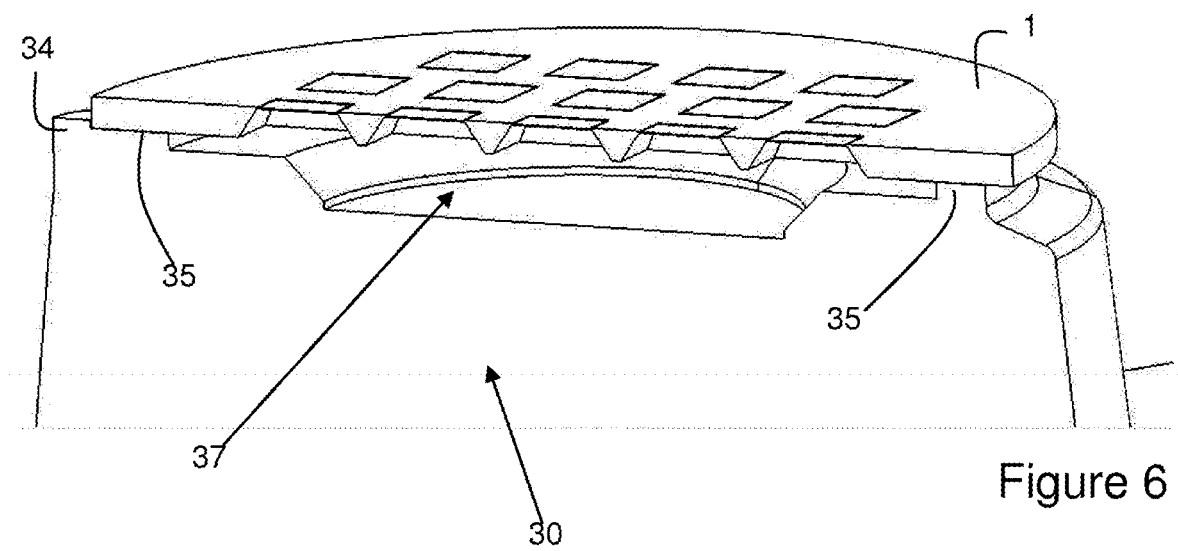
FIGS. 6, 7 and 8—detail views of elements of male and female parts of the injection moulding tool in relation to a membrane placed therein.

FIGS. 4 and 5 illustrate a male part 30 of an injection moulding tool adapted to form a well insert 10 according to the invention, and FIG. 6 illustrates a cutaway view of the male part 30 with a membrane 1 placed thereupon, the cut passing diametrically through an abutment. The majority of the features of the mould, such as the protrusions for forming openings 14, are standard and need not be described further. Male part 30 of the mould protrudes from a face 31 of the mould, as is generally known. Face 31 of the mould comprises a deep melt distribution groove 32 and with three melt outlets 33 leading from the melt distribution groove 32 to the cavity formed when the mould is closed and which will become the membrane support 10*a* once moulded. Other numbers of melt outlets are of course also possible. Melt outlets 33 are evenly distributed around the mould, and ideally are of the same number as the abutments 34 (see below) which will form notches 18 in the finished well insert 10. Furthermore, each melt outlet 33 is ideally aligned with a corresponding abutment 34 to minimise the formation of voids adjacent to the abutments 34, although it is possible to arrange the melt outlets differently. However, arranging them in line with each other causes the melt to flow evenly and symmetrically around each side of each abutment 34, and thus minimises any unbalanced forces applied to the membrane 1 by the flowing of the melt.

Abutments 34 are provided adjacent to a support surface 35, upon which the membrane 1 is positioned for injection moulding. These abutments 34 are situated radially outboard of the support surface 35, and extend perpendicularly to the support surface 35 in such a manner as to contact the cylindrical sidewall 1*p* of a membrane 1 placed upon the support surface 35. In the illustration of FIGS. 4 and 5, support surface 35 is annular and extends around the free end of the male part 30 of the injection moulding tool, as well as radially towards each abutment 34. Aside from around each abutment 34, the membrane 1 protrudes outwards from support surface 35, as can be more clearly seen in FIG. 6. The lateral surface 34*a* of each abutment 34 is curved so as to closely follow the outer surface 12*a* of the membrane 1, with sufficient play to enable the membrane 1 to be placed therein easily without damaging it. A play of 15-35 µm, preferably 20-30 µm, ideally substantially 25 µm is sufficient.

Figure 7:
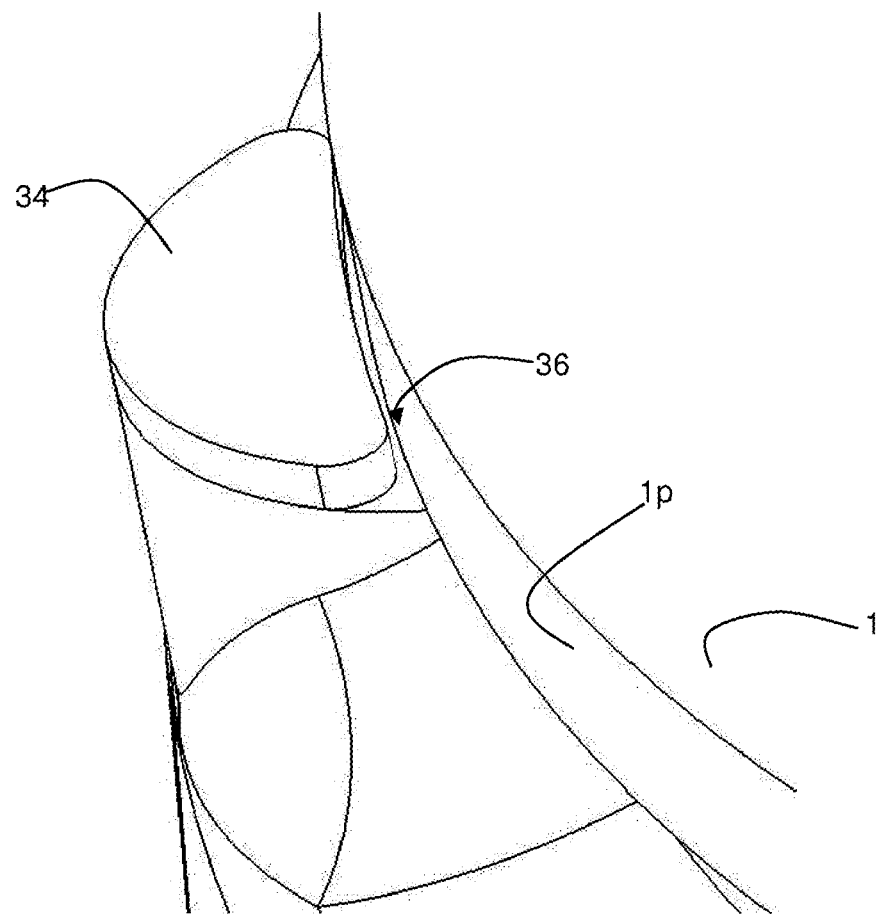

This play 36 is visible on FIG. 7, between abutment 34 and membrane 1. Also visible on FIG. 7 is the height of abutment 34 over the support surface 35. This height should be kept to a minimum so as to ensure maximum contact around the periphery 1*p* of the membrane 1 with the plastics material of the membrane support 10*a*. However, the material of the membrane is significantly harder than the metal material of the male part of the mould 30, and hence wear of the abutments 34 is an issue, as is their machinability. In practical terms, a height of 0.075-0.2 mm is adequate. In terms of sealing, a relative height between the abutments 34 and the thickness of the membrane 1 of 1:20 to 1:5, ideally 1:10 is again adequate.

Inside of support surface 35 is relieved so as to provide a recess 37. In order to position and gently hold the membrane 1 while the injection moulding tool is being closed, a vacuum line (not illustrated) may be provided opening into recess 37, however this is not obligatory.

Figure 8:
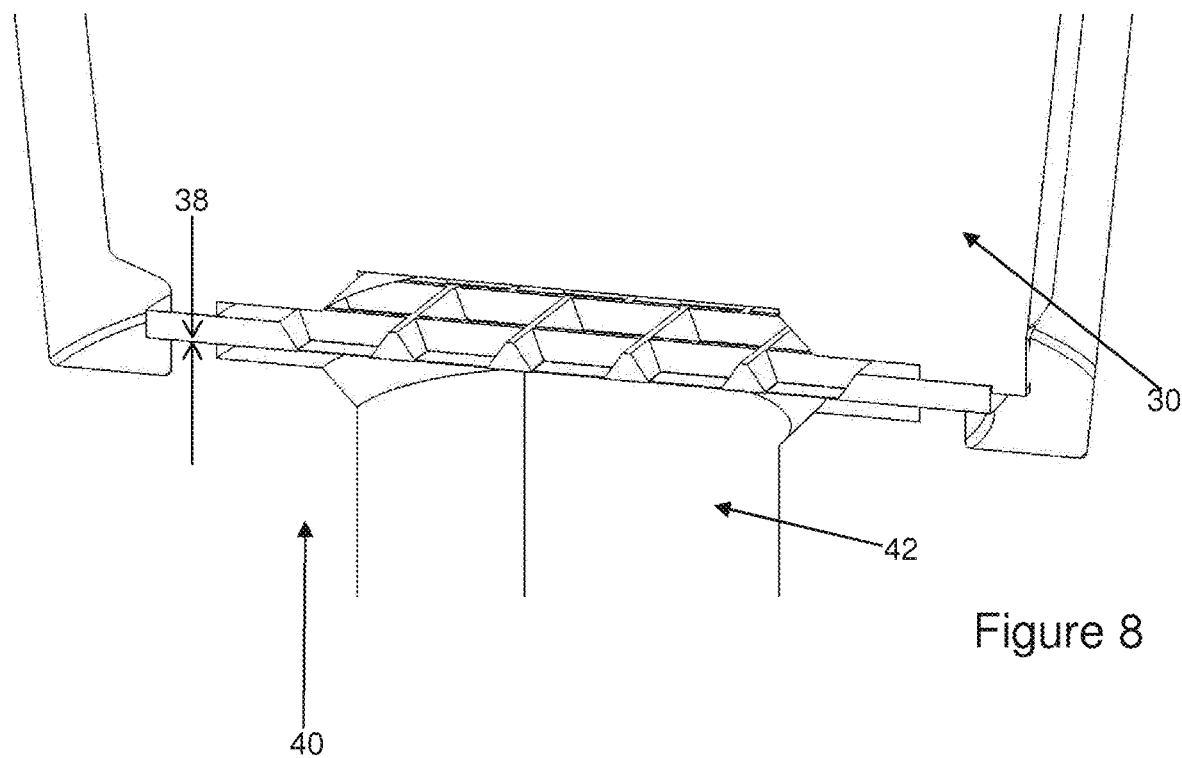

FIG. 8 illustrates a cutaway view of a complete and closed injection moulding tool, with a membrane 1 placed therein. This view is in the opposite orientation to that of FIGS. 5-7. The entire tool comprises not only male portion 30 as described above, but also female portion 40.

When the male 30 and female 40 part of the injection moulding tool are closed on the membrane 1, an axial play 38 is present between the membrane 1 and the female 40 or male 30 part of the tool, depending on the orientation of the tool and whether a vacuum is present or not. This play 38 is ideally between 1 and 5 µm, preferably between 1.5 and 2.5 µm.

The play 38 has several functions. Firstly, it prevents the tool, when closed, from crushing the membrane 1. Secondly, it permits air to escape through a vent 42 provided for this purpose in the female part 40 of the injection moulding tool. Additionally or alternatively, such a vent can be provided in the male part 30 of the tool. Since, as is clear from the figures, the cavity formed between the two parts 30, 40 of the injection moulding tool is filled from the wider end, i.e. the end that forms the flange 11 of the well insert 10, air will be displaced and must exit from the membrane 1 end of the cavity in an even fashion to prevent air bubbles forming. Air bubbles are not only undesirable manufacturing flaws, but they can result in differential forces being applied to the membrane 1 due to irregular melt flow, potentially twisting or bending membrane 1 and thus destroying it.

It should further be noted that there also exists a risk of damaging the well insert 10 due to careless handling while extracting it from the mould. To minimise this risk, the sidewall 13 of the first intermediate section is provided with a taper of 7-8°. This range has proved optimal for this application.

Since membrane 1 is not only brittle but is very hard, and certainly harder than the material of the injection moulding tool, abutments 34 can be subject to wear due to the membrane 1 rubbing thereagainst when it is positioned on the male part 30 of the injection moulding tool, and during injection of the plastics material.

Figure 9:
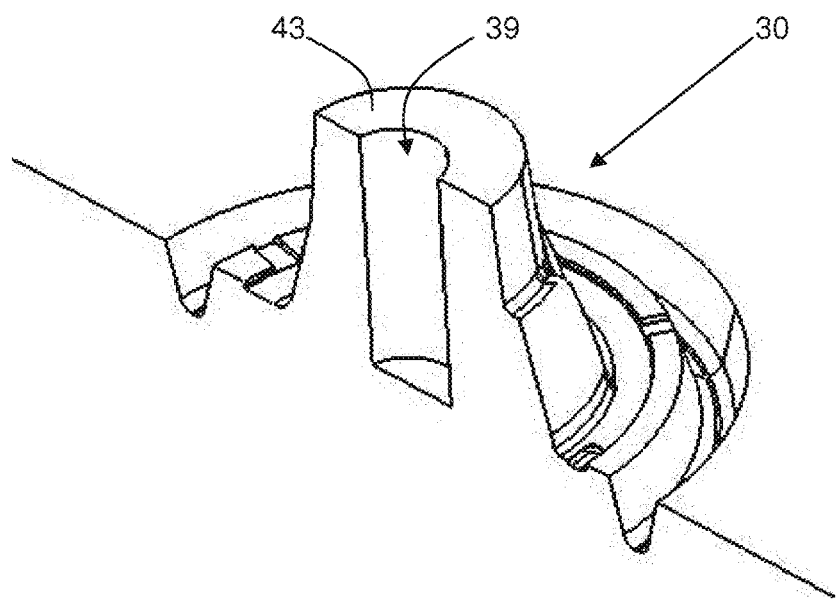
FIG. 9—a variant of a male part of an injection moulding tool.
Figure 10:
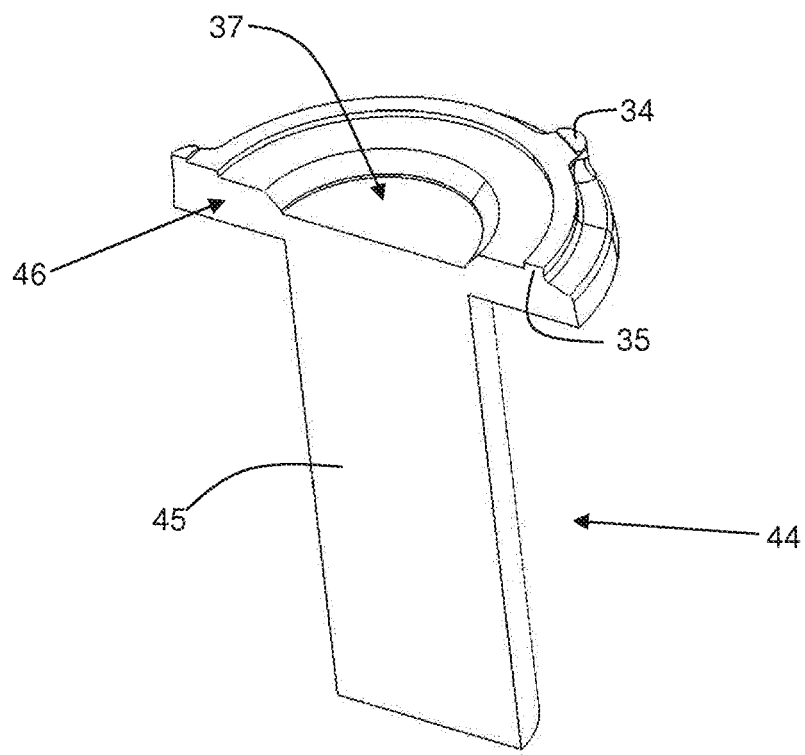
FIG. 10—an insert for the male part of an injection moulding tool of FIG. 9.

FIGS. 9 and 10 illustrate a modification to the male part 30 of the injection moulding tool which permits replacement of the abutments 34 without requiring reworking of the entire tool.

As can be seen in FIG. 9, the male part 30 the injection moulding tool comprises a bore 39, and terminates in an end surface 43. As illustrated, and surface 43 is flat, however it may also be convex, concave, undulating, crenellated or any other convenient shape. And surface 43 may be provided with positioning means such as pins, lugs, crenelations or similar so as to angularly position an insert 44.

Insert 44 is provided with a stem 45 sized to extend down bore 39, stem 45 being coaxial with insert head 46 which carries abutments 34, support surface 35 and recess 37 as defined above.

Insert 44 may also be positioned on the male part 30 of the injection moulding tool e.g. by pinning, threading, or any other convenient positioning means.

Thus, in the case of excessive wear of abutments 34, insert 44 can simply be replaced.

Figure 11:
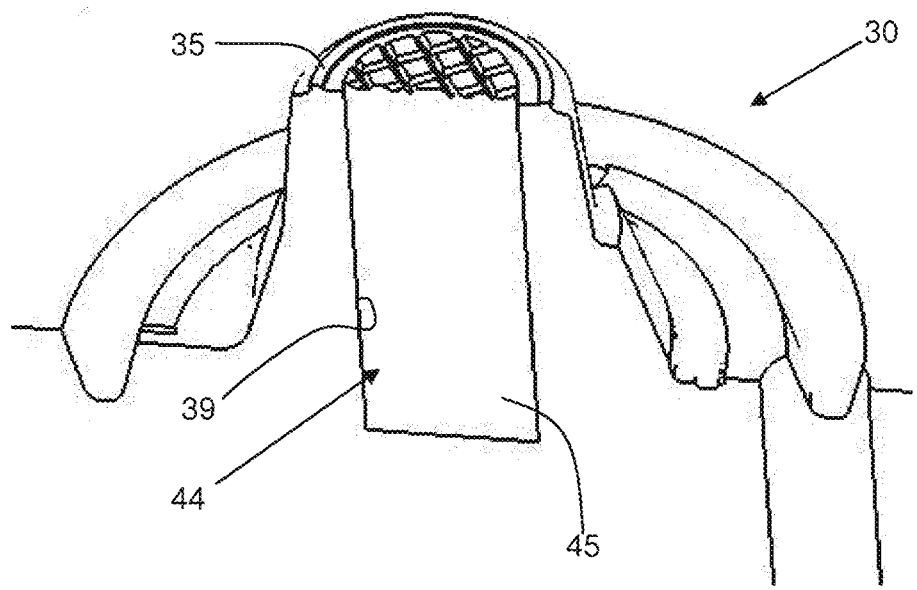
FIGS. 11 and 12—views similar to FIGS. 9 and 10 respectively showing a variant of a male part of an injection moulding tool.
Figure 12:
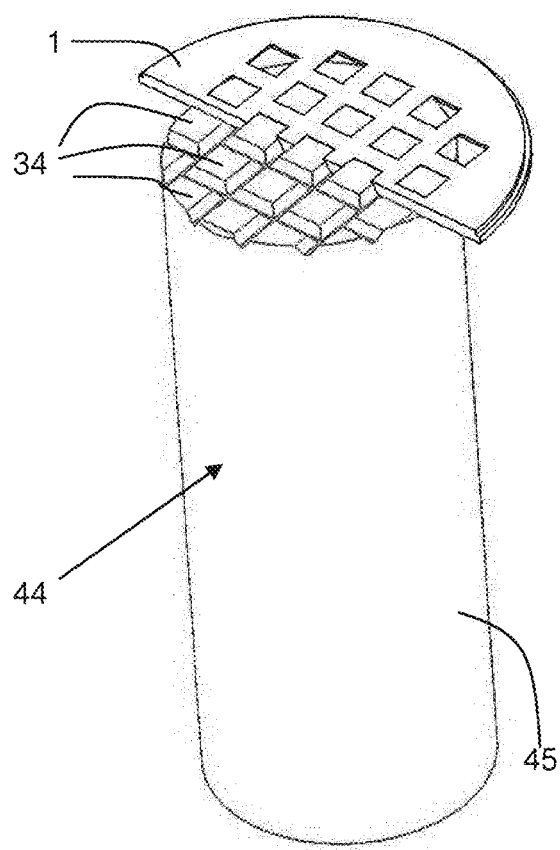

FIGS. 11 and 12 illustrate an alternative arrangement of insert 44. In this variant, male part 30 of the injection moulding tool retain support surface 35, and abutments 34 are formed directly on insert 44 in the form of lugs shaped so as to fit closely inside the recesses formed by frame elements 1c and thinner portions 1b of the membrane 1, as illustrated in FIG. 1. In FIG. 12, membrane 1 has been cut along its diameter so as to illustrate this principle.

In such case, insert 44 may be made of the same or similar material to the rest of the male part 30 of the injection moulding tool, or may be made of a softer material such as a plastic. It is also conceivable that insert 44 may be made of a harder material such as a ceramic which is sufficiently hard so as not to be subject to wear from contact with the membrane 1. For instance, a sintered ceramic material would be suitable, and may be bonded into bore 39 with a suitable adhesive.

When using such an insert, no notches 18 are present in the finished well insert is due to the absence of abutments 34 situated outside of the support surface 35. In such a case, opposing flange 17 extends along the entirety of the periphery of the membrane 1 and is thus annular.

Figure 13:
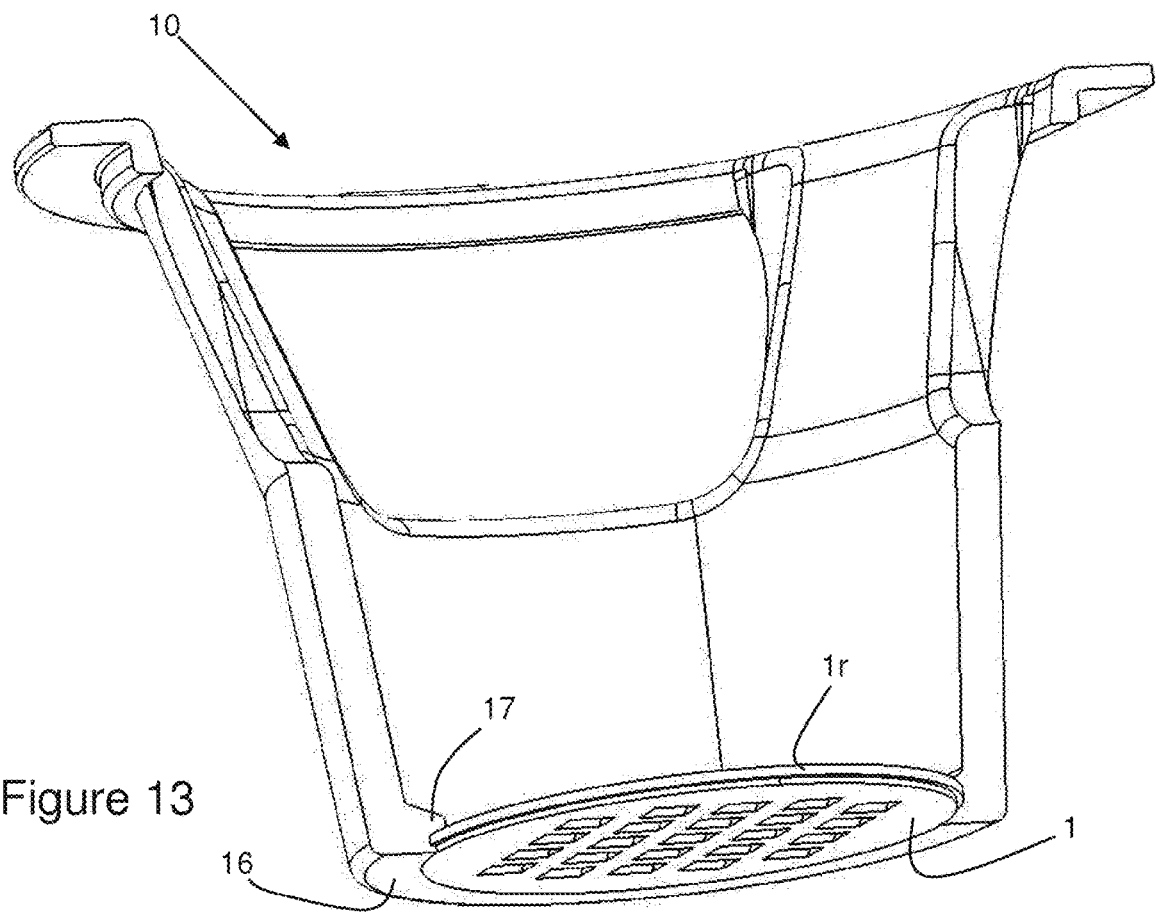
FIGS. 13, 14 and 15—cutaway views of further variants of well inserts according to the first embodiment in which the lower surface of the membrane is flush with the lower surface of the membrane support.
Figure 14:
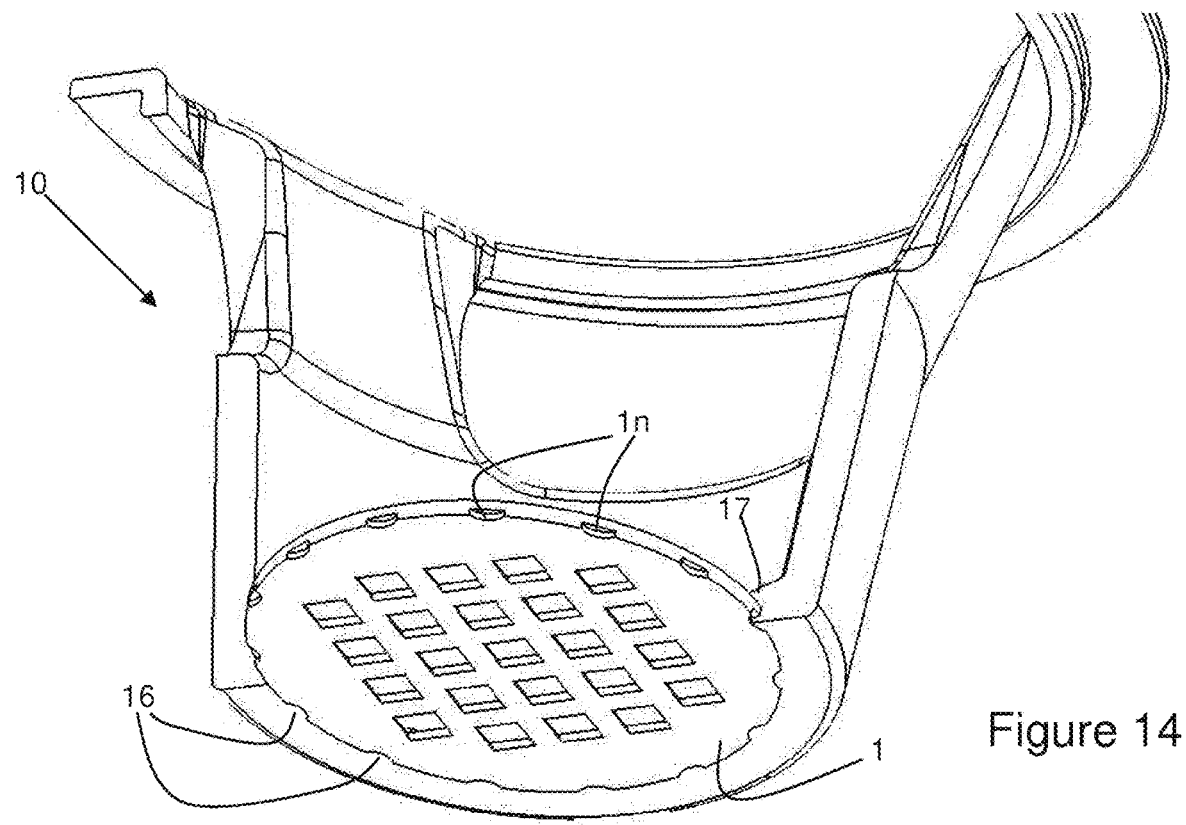

For cases in which a recessed membrane is undesirable, it is also possible to arrange the lower surface of the membrane 1 to be flush with the lower surface of membrane support 10a. FIGS. 13 and 14 illustrate 2 variants of such an arrangement.

In FIG. 13, membrane 1 is provided with an annular rim 1r arranged extending around an upper side thereof. Annular flange 16 of the membrane support 10a and thus extends around the periphery of membrane 1 up to the full-thickness section so as to hold the membrane 1 between annular flange 16 and one or more opposing flanges 17 situated on the upper side of membrane 1, the number of opposing flanges depending on which of the above-mentioned arrangements of abutments 34 is used.

In FIG. 14, membrane 1 is provided with a plurality of peripheral notches 1n spaced at substantially equal annular intervals around the periphery on the lower face of the membrane 1. Once moulded, a plurality of flanges 16 are formed extending into the corresponding peripheral notches 1n, thereby supporting the membrane 1 between these flanges 16 and one or more opposing flanges 17 as above.

For the membranes 1 illustrated in FIGS. 13 and 14, annular rim 1r and peripheral notches 1n may be formed e.g. by etching, laser machining, or grinding.

Figure 15:
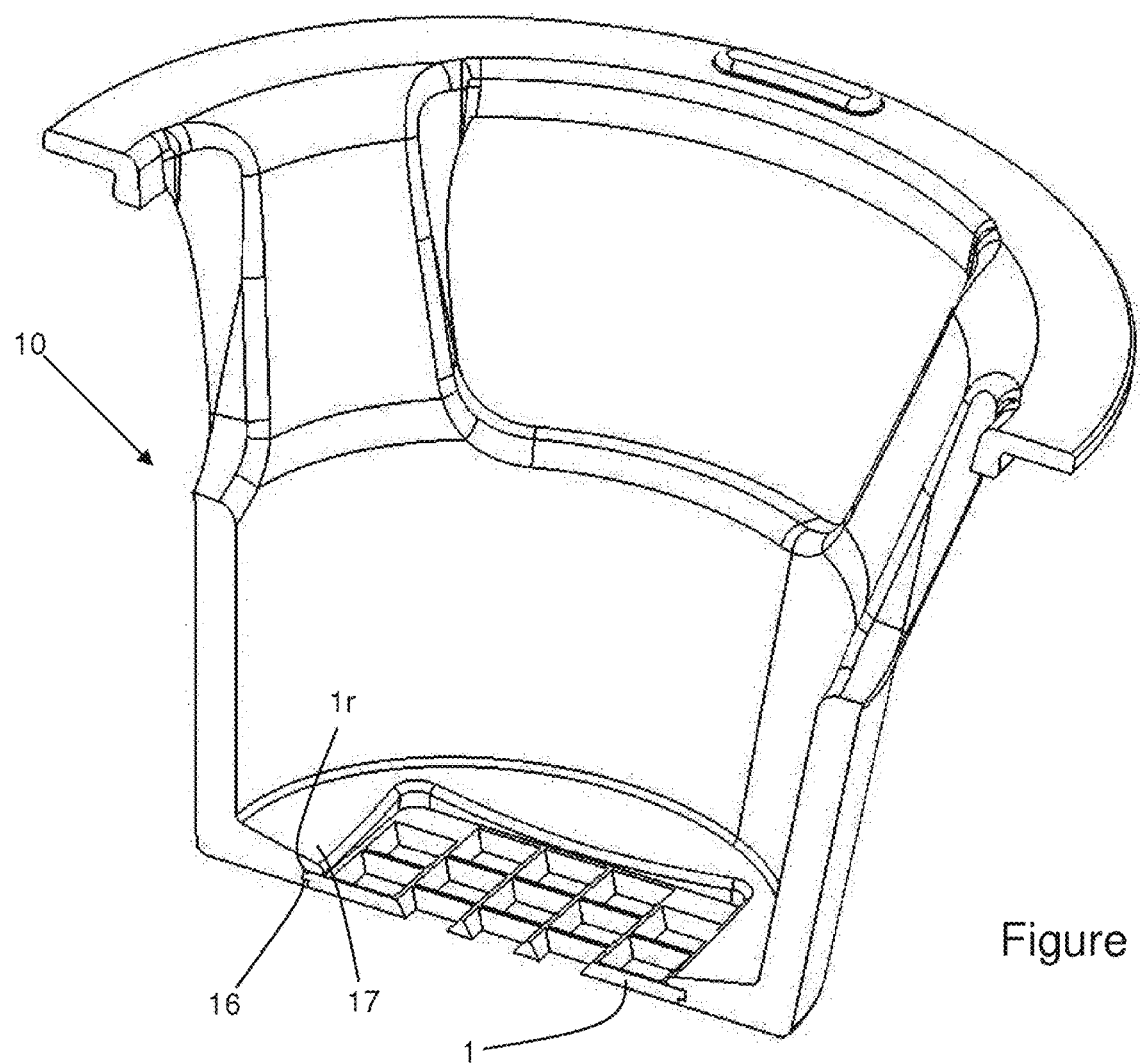

FIG. 15 illustrates yet further flush-membrane variant, adapted for a square membrane 1. Square membranes 1 are interesting from a manufacturing perspective, since many more of them can be fitted onto a single wafer of silicon, a silicon nitride or similar, and they can very easily be separated therefrom simply by cutting the wafer in straight lines.

In the variant of FIG. 15, the membrane 1 is provided with a peripheral rim 1r, in a similar fashion to FIG. 13, and no notches 18 are present in the membrane holder 10a. Flanges 16 and opposing flanges 17 are thus rectilinear, following the periphery of membrane 1.

Alternatively, peripheral notches 1n as in FIG. 14 may be used, and membrane 1 may be positioned on the male part 30 of the injection moulding tool by abutments 34 similar to those illustrated in FIGS. 4-7 and 10 but numbering four and being situated either at the midpoint of the sides of membrane 1 or at the corners of membrane 1, thereby resulting in corresponding notches 18 being present in the finished well insert 10.

In order to create such a flush-fitted membrane, particular adaptation of the female part 40 of the injection moulding tool is required to prevent the lower face of the well insert 10 from being convex, with the membrane 1 protruding outwards. This is caused by the shrinkage of the material back towards the upper end of the well insert 10 during cooling of the plastics material during moulding. Such protrusion of the membrane 1 is not only undesirable from an aesthetic perspective, but it can also reduce the quality of the sealing between the membrane 1 and the membrane holder 10a, as the flange 16 is pulled backwards and outwards, and the cylindrical wall 12a of plastics material which should be in intimate contact with the peripheral wall 1e of the membrane 1 is likewise pulled backwards and outwards.

Figure 16:
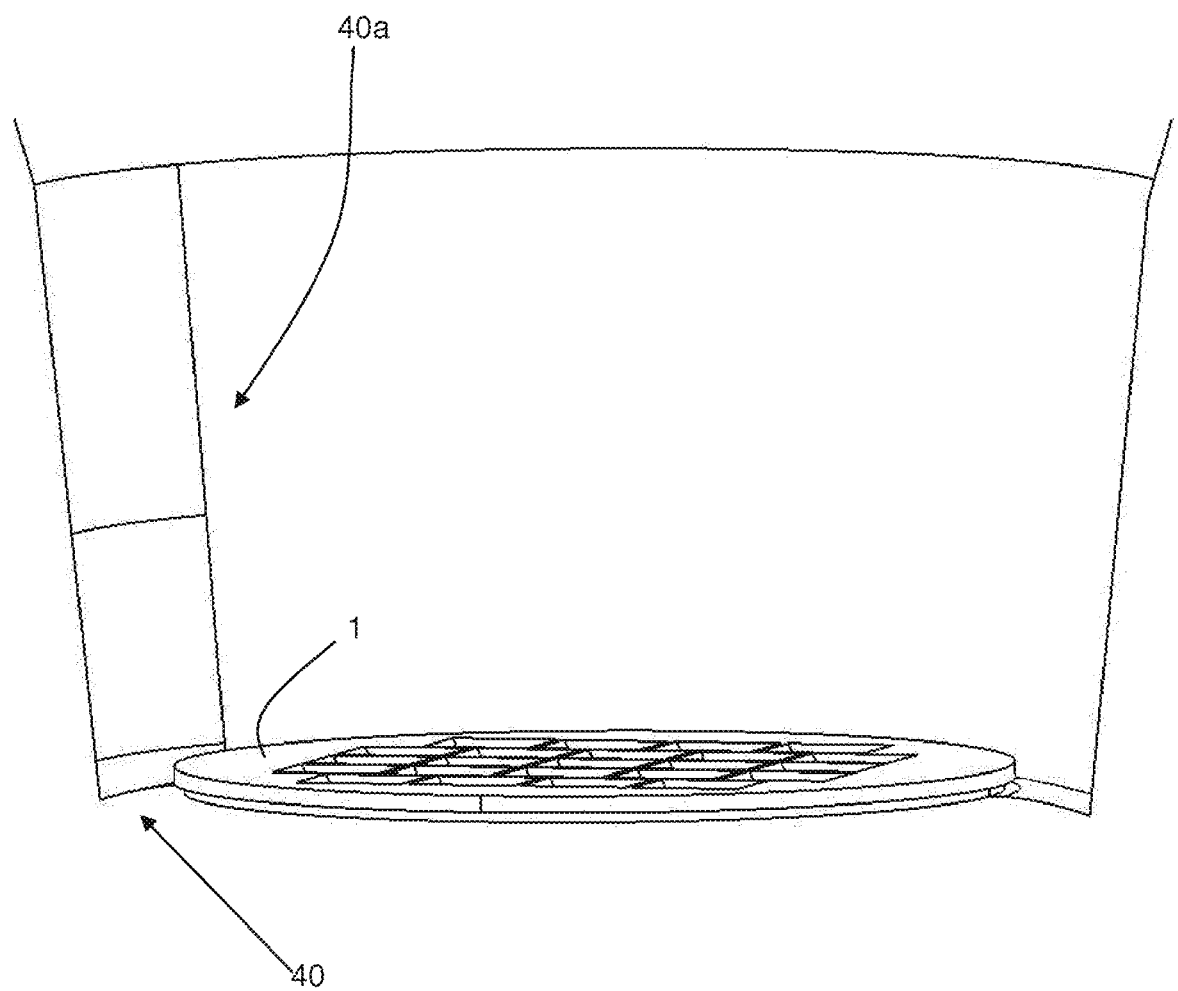
FIG. 16—a cutaway view of a female part of an injection moulding tool for producing a well insert as illustrated in FIG. 13 or 14.

To solve this problem, the female part 40 of the injection moulded tool is formed as illustrated in FIG. 16. In essence, the cavity 40a in the female part 40 surrounding the membrane 1 extends away from the membrane 1 (illustrated here for reference) such that, before the plastics material cools, membrane 1 is recessed from the end face of well insert 10. The extent to which the cavity 40a extends ahead of the membrane 1 is calculated such that, upon cooling of the plastics material to room temperature, the lower end face of the well insert 10 is absolutely flush and flat. This calculation depends on the properties of the plastics material chosen, the temperature of the melt, and the shape of the well insert 10. Based on these parameters, the person skilled in the art can make the required calculations.

It should be further noted that the same principle applies to a two-piece well insert of the SNAPWELL™-type. In such a case, the membrane 1 is integrally moulded to a first element of the membrane support 10a which attaches to a second element constituting a separate hanger so as to form the entire well insert, in the manner known for the SNAP-WELL™.

Embodiment 2: Direct Fastening

FIGS. 17a-18h illustrate an alternative principle for joining the membrane 1 to the membrane support 10a so as to form a well insert according to the invention.

Figure 17A:
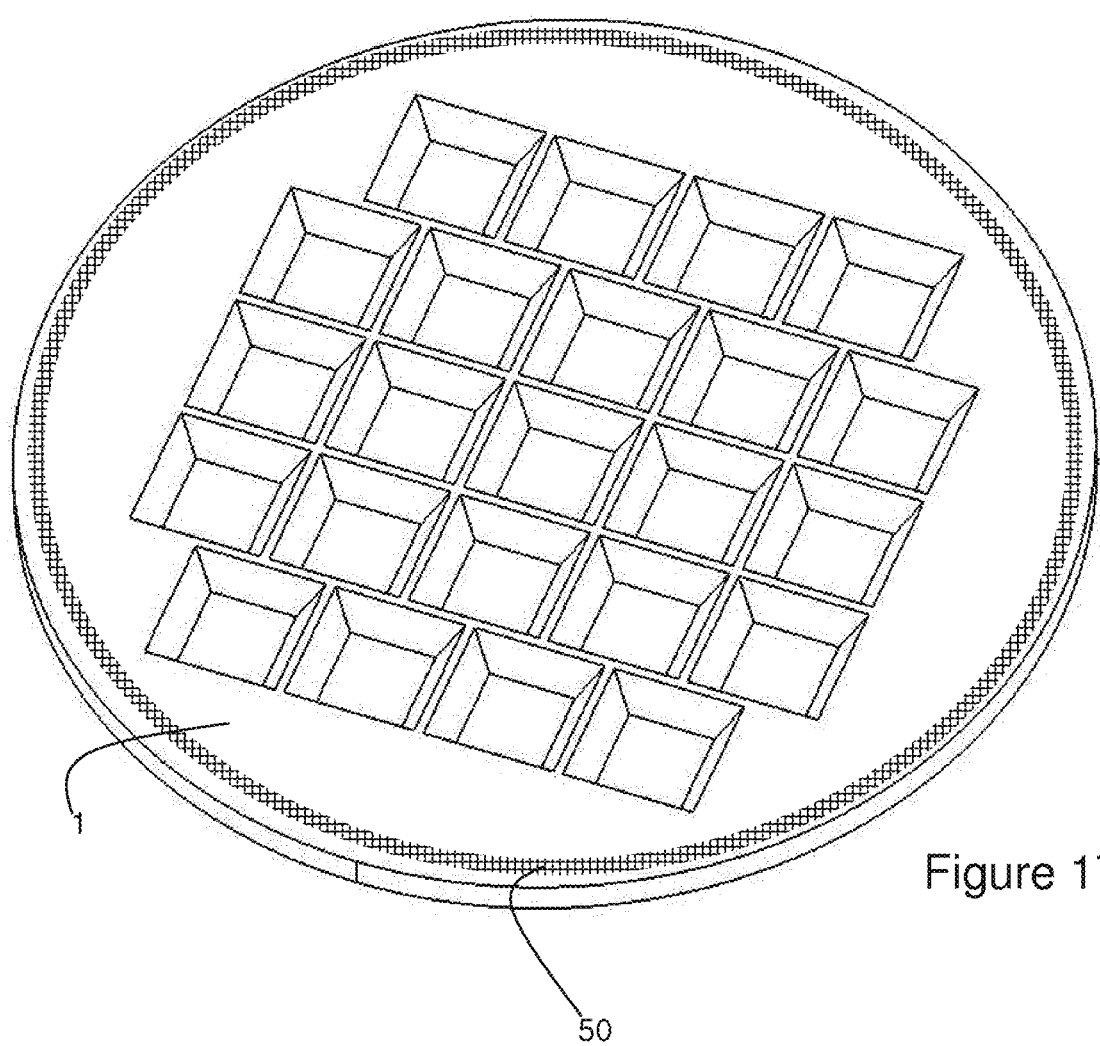
FIG. 17a—a membrane specifically adapted for producing a well insert according to the second embodiment.

FIG. 17a illustrates, in a view similar to FIG. 1, a membrane 1 adapted for fastening to a membrane support 10a by melting said membrane support partially for it to fill surface features, in particular microstructures, arranged in the membrane to provide pinning or nailing of the support to the membrane and solid attachment therebetween upon cooling of the molten material without any external linking element. While melting is generally known for attaching plastic parts to hard part is, e.g. ceramics, glasses, glass-ceramics and so on, to the best of the applicants knowledge it has never been applied for construction of a well insert 10.

Examples of such joining are given in the documents EP2061589, EP2735432, and US2011232826. In essence, such methods permit joining a plastic part to a hard part without use of any third-party mediators such as glue, solder, intermediate metallic layers, or similar, by bringing two parts into contact and then causing the material of one of the parts to melt and thereby weld itself to the other part.

Membrane 1 is similar to that of FIG. 1, except that it comprises a joining zone 50 situated at or near its periphery on the upper surface thereof. Joining zone 50 is structured by any convenient process such as machining, grinding, laser etching, wet etching, reactive ion etching, anisotropic etching of microstructures, and so on. Examples of such anisotropically etched microstructures particularly suited for well inserts will be described in more detail below. Although the membrane 1 has been illustrated as being circular, a square membrane as illustrated in FIG. 15 is particularly suitable in the case of anisotropically etched structuring, due to straight lines being easier to etch than curves.

Figure 17B:
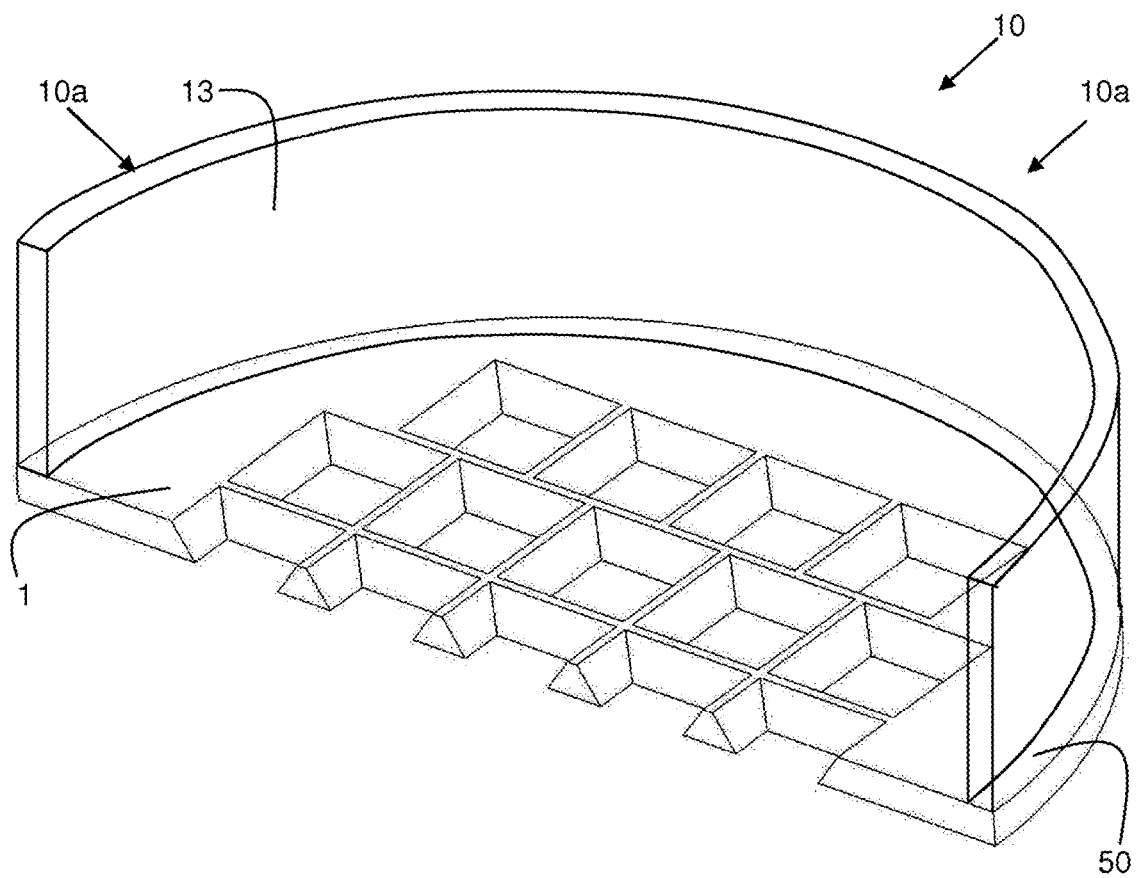

FIG. 17b illustrates, in a partial, transparent cutaway view, a schematic view of membrane 1 of FIG. 16 joined to sidewall 13 of the 1$^{st}$ intermediate section of membrane support 10a. The remainder of the membrane support 10 may be constructed as that illustrated for the 1st embodiment, and has not been illustrated here. Furthermore, even though sidewall 13 has been illustrated here as being cylindrical, it may also be tapered as in the 1$^{st}$ embodiment.

Sidewall 13 is joined to the joining zone 50 of membrane 1 by directly thermally welding the sidewall 13 to the joining zone 50. This can be achieved, as is generally known, by heating, e.g. by means of a laser directed through the membrane or from the side, ultrasonic vibrations, or direct application of heat, which causes the lower end of sidewall 13 to soften and adhere to the structure and texture of joining zone 50. To assist in this joining, the lower end of sidewall 13 may be provided equally with structures such as illustrated in EP2735432, referenced above.

Suitable materials for the membrane support 10a embodiment are polystyrene and polycarbonate, although of course other plastics materials such as polyolefins are also possible.

FIGS. 18a-j illustrate variants of structuring joining zone 50, in cross-section. These variants apply equally well to both circular and square/rectangular membranes 1. In the case of circular membranes, the features illustrated can be presumed to be cylindrically symmetrical, or symmetrical with a certain order of symmetry (e.g. greater than twelve) if the features are formed as facets rather than as smooth curves around the periphery of the membrane. If a feature is microfabricated with an anisotropical method, the anisotropy will impose the orientation of the feature locally, e.g. the crystal structure of silicon may favour four symmetrical orientations of a feature, which does not impede its global arrangement with higher symmetry.

Figure 18G:
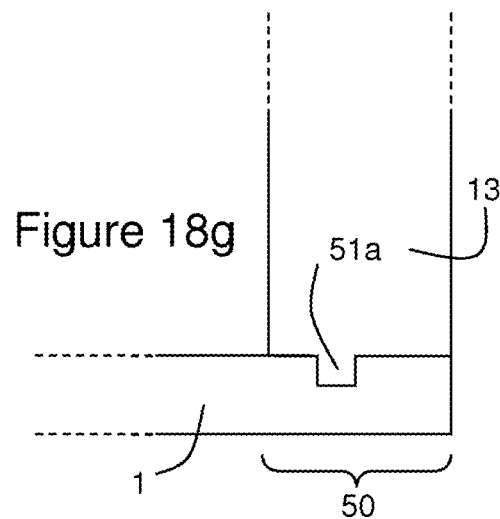

FIG. 18a shows a single protruding ridge 51 of rectangular cross-section, and FIG. 18g shows a single cavity 51a, both of which can e.g. formed by isotropic etching (e.g. reactive ion etching (RIE), deep reactive ion etching (DRIE) or similar) using a mask of e.g. silicon nitride which is then subsequently removed. Ridge 51 or cavity 51a assist in bonding by providing increased surface area, and also improved sealing. Although ridge 51 and cavity 51a have been illustrated as being off-centre towards the inside of the well insert 10, they may be situated on the centreline of sidewall 13, or even off-centre towards the outside of the well insert 10. Ridge 51/cavity 51a extend around the entire periphery of the membrane 1, and may be interrupted to provide improved adhesion or improved sealing.

Figure 18H:
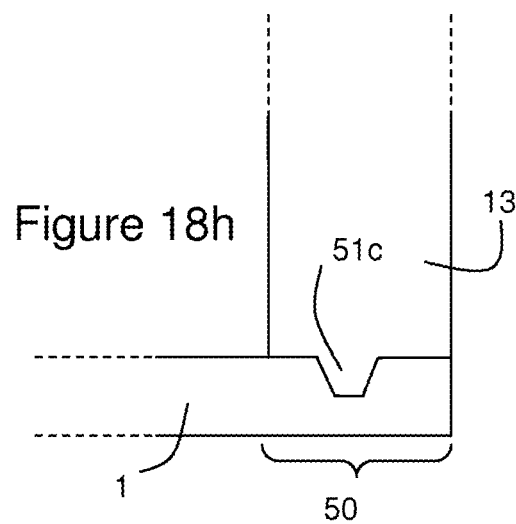

FIG. 18b shows an embodiment with a pair of protruding ridges 51, further improving sealing. Naturally, this also applies to cavities 51a, or to a mixture of ridges 51 and cavities 51a FIG. 18c illustrates an embodiment in which the protruding ridge 51 is of trapezoidal cross-section, and FIG. 18h shows a cavity 51c similarly of trapezoidal cross-section, formed e.g. via anisotropic etching (plasma etching, wet etching, or similar) using a mask 52 of e.g. SiN or SiO$_2$. In the example of FIG. 18c, the mask 52 has not been removed.

FIG. 18d illustrates an embodiment in which, instead of a protruding ridge, and undercut "lock" structure 53 is provided, again extending around the entire periphery of membrane 1. Formation of such structures by isotropic etching of a straight-sided cavity by means of a mask and e.g. RIE or DRIE followed by anisotropic etching by e.g. plasma etching or wet etching along the <111> crystal planes is generally known and need not be discussed further.

FIG. 18e illustrates a combination of an undercut "lock" structure 53 towards the inside, and a protrusion 51 to the outside of the joining zone 50. Naturally, the structures may be provided in the opposite arrangement.

FIG. 18f illustrates a variant in which two undercut "lock" structures 53 are provided adjacent to one another, so as to form a ridge 56 between them. This ridge 56 forms an excellent seal. As illustrated, the material of the sidewall 13 has been melted to a greater extent than in the preceding variants, so as to form radiuses 54 on either side of the sidewall 13. Excess material 55 can flow into the outermost "lock" structure 53. A third "lock" structure may also be provided on the inside of the well insert 10, i.e. to the left of the sidewall 13 in the illustration of FIG. 18f.

Figure 18I:
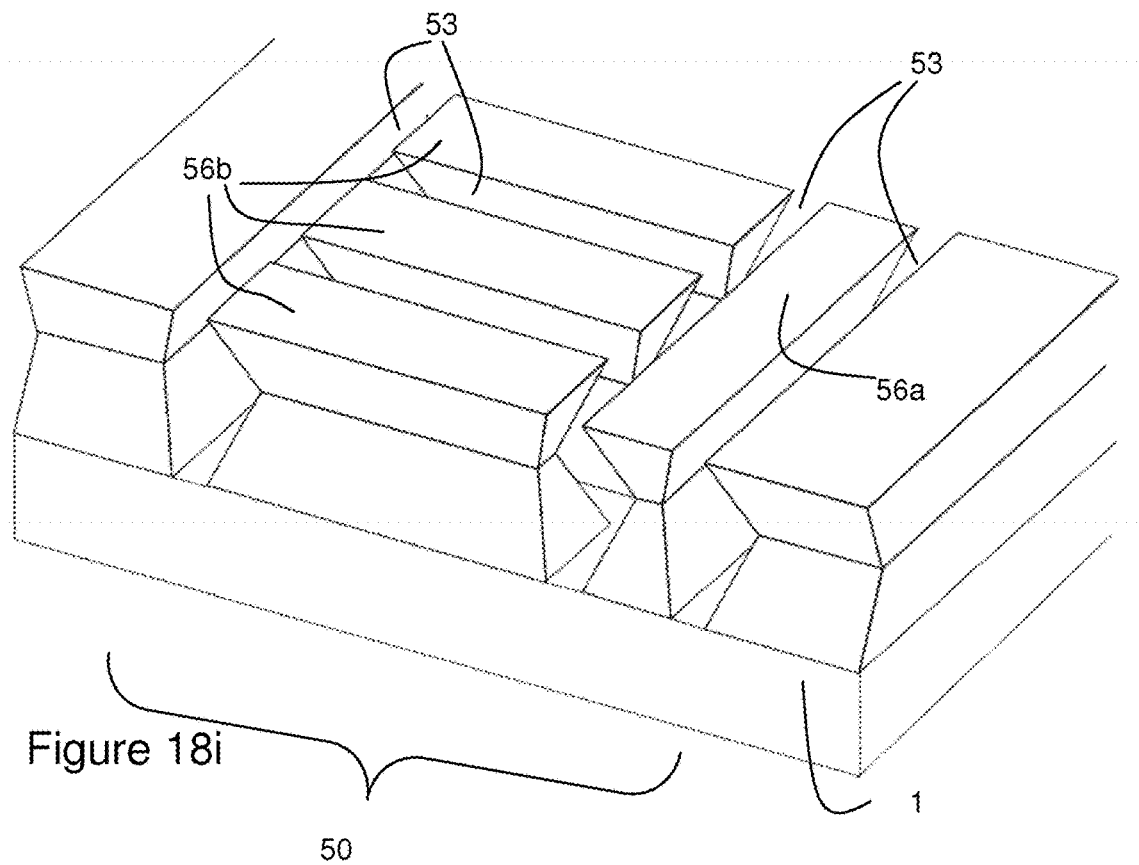

FIG. 18*i* illustrates just the joining zone 50 of a membrane 1, which is provided with a more complex etched structure. This etching is carried out by means of appropriate masks so as to create a series of interconnecting "lock" structures 53 leaving ridges 56*a*, 56*b* therebetween. Ridge 56*a* is similar to ridge 56 of FIG. 18*f*, and extends around the periphery of the membrane 1 on the outer side of ridges 56*b*. Ridge 56*a* serves as the primary seal. Ridges 56*b* are mutually parallel, and are arranged perpendicular to ridge 56*a*, and serve primarily for anchoring the sidewall 13 to the membrane 1.

Figure 18J:
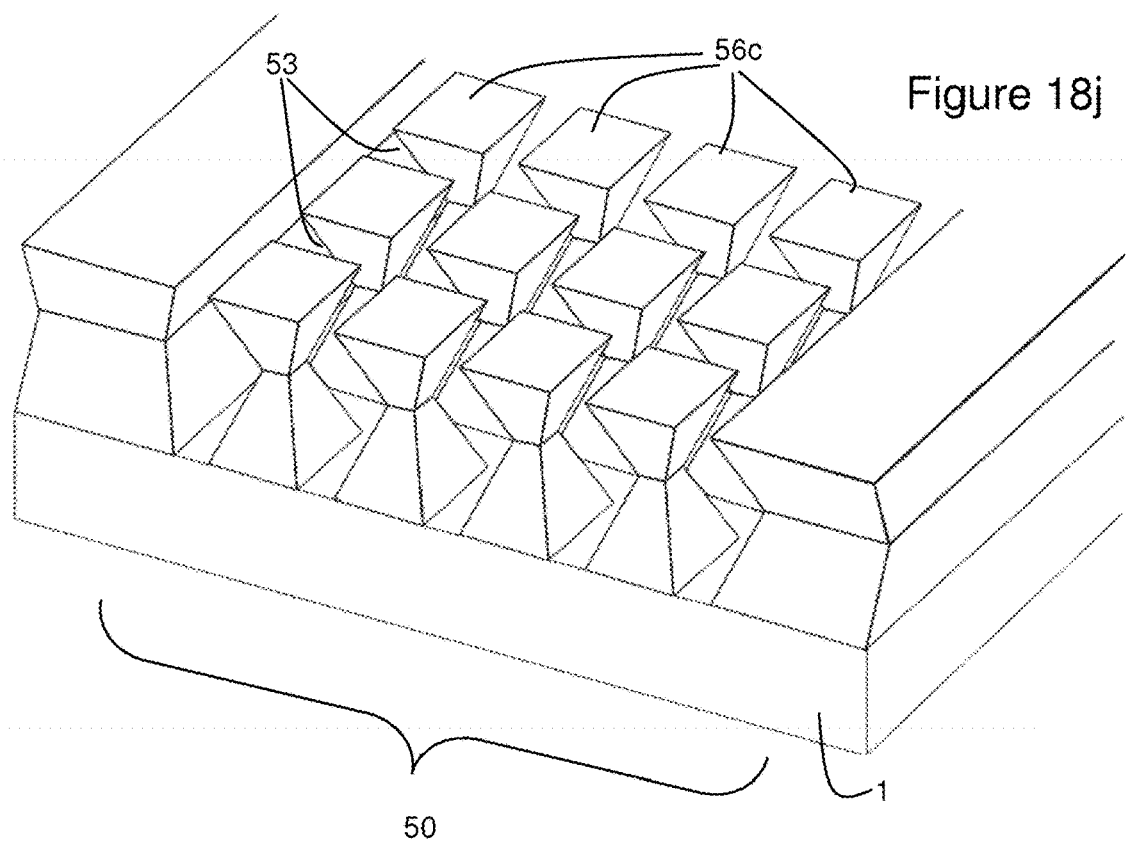

Finally, FIG. 18*j* illustrates a variant in which interconnecting "lock" structures 53 are formed in a grid pattern so as to leave an array of protuberances 56*c*.

Third Embodiment: Clipping

Figure 19:
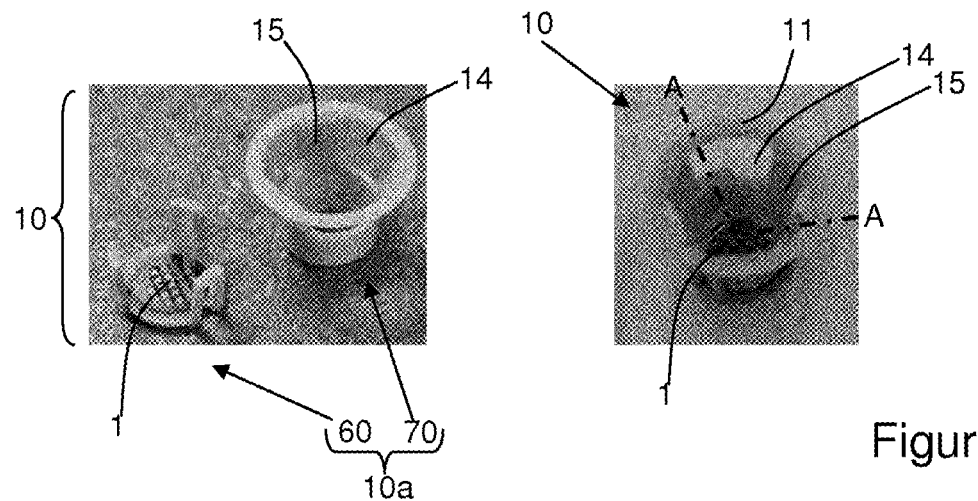
FIGS. 19 and 20—photographs and a cross-sectional schematic view of a well insert according to the third embodiment of the invention.
Figure 20:
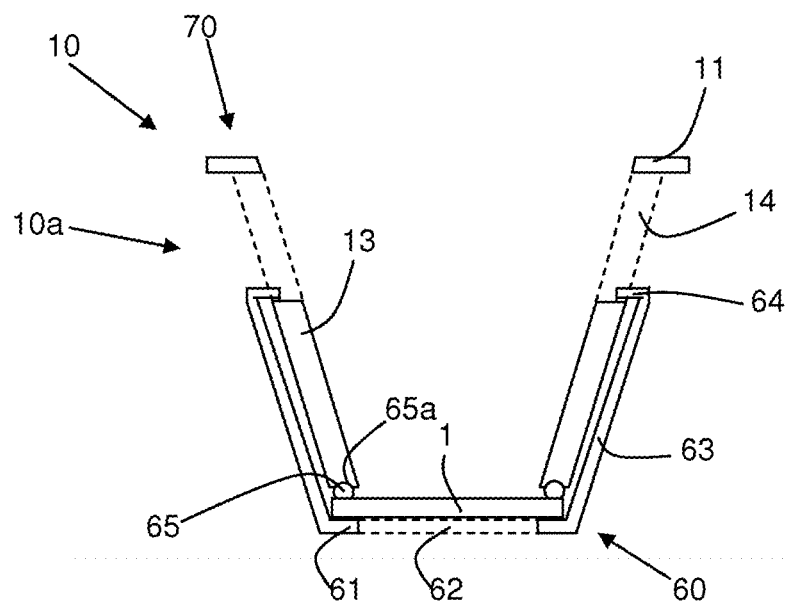

FIGS. 19 and 20, illustrate a third embodiment of a well insert 10 according to the invention, the left-hand image of FIG. 19 showing well insert 10 in disassembled form, and FIG. 20 showing schematically a section along A-A of FIG. 19.

Well insert 10 according to this embodiment comprises a membrane support 10*a* formed in two parts, namely hanger 70 and end piece 60. Hanger 70 is constructed in a similar fashion to the entire membrane support 10*a* as shown in FIGS. 2, 13 and 14, except that it does not integrally comprise the membrane 1. However, other features such as sidewall 13, openings 14, connecting elements 15, flange 11 etc. remain substantially similar. Indeed, hanger 70 may also be a Corning SNAPWELL™ hanger, or any other commercially available hanger.

Membrane 1, which is of the type as described above, is positioned against the lower end of sidewall 13 by means of an end piece 60, and is sealed thereto by means of a seal 65. As illustrated, seal 65 is a separate piece arranged in an annular groove 65*a* extending around the lower end face of hanger 70, although it may be a seal integral with the sidewall 13, e.g. by being formed of a sufficiently soft elastomeric material co-moulded with the sidewall 13. Seal 65 may also be a simple flat seal, which does not require an annular groove 65.

The membrane 1 is held in sandwich between a flange 61 of the end piece 60, which extends inwards leaving an opening 62 to permit fluid access to the surface of the membrane 1. End piece 60 is thus situated on the outside of hanger 70.

End piece 60 comprises a plurality of arms 63 extending towards openings 14, which terminate in first clipping elements 64 such as hooks or lugs, adapted to interface releasably with the lower edges of corresponding openings 14, which constitute corresponding second clipping elements. Alternatively, the second clipping elements may comprise one or more lugs, rims, recesses or other features may be provided extending into or out from the structure of hanger 70, which are shaped so as to interface with corresponding first clipping elements provided on arms 63. As illustrated, these first clipping elements 64 are hooks engaging with the openings 14.

The length of the arms 63 and the position of the clipping elements 64 are chosen so as to, in the assembled state, compress seal 65. This not only seals the periphery of membrane 1 to the hanger 70, but also serves to keep the arms 70 in tension and the attachment means 64 engaged. It is also possible that arms 70 provide an elastic force in addition.

In essence, end piece 60 thus clips onto hanger 70 so as to maintain the membrane 1 in place, while permitting easy removal thereof by unclipping the end piece 60 from the hanger 70.

This permits the well insert 10 to be disassembled for cleaning the membrane 1 for re-use.

Although the invention has been described in reference to various concrete embodiments as described above, these are not to be considered as being limiting to the scope of the invention. Further variants are possible without departing from the scope of the invention as defined in the appended claims.

The invention claimed is:

1. A well insert (10) for cell culture, comprising:
    a membrane support (10*a*) having an upper end and a lower end, said upper end being adapted to engage a well of a microplate so as to suspend the well insert (10) therein; and
    a permeable membrane (1), transparent in both air and water, for supporting a tissue culture, the permeable membrane (1) being attached at said lower end of the membrane support (10*a*) and sealed thereto, the permeable membrane (1) being ceramic and having a thickness less than 10 µm,
    wherein the membrane support (10*a*) is overmoulded on to the permeable membrane (1) such that the permeable membrane (1) is integrally moulded into a structure of the membrane support (10*a*),
    wherein the membrane support (10*a*) also has a first flange (16) in contact with a first side of the permeable membrane (1), and an opposing second flange (17) in contact with a second side of the permeable membrane (1), said second side being opposite said first side,
    wherein the membrane support (10*a*) is made of a polyolefin material.

2. The well insert (10) according to claim 1, wherein the membrane support (10*a*) is directly sealed to the permeable membrane (1).

3. The well insert (10) according to claim 1, wherein said opposing second flange (17) is continuous or is formed as a plurality of opposing flanges (17) separated by notches.

4. The well insert (10) according to claim 1, wherein said first flange (16) is continuous or is formed as a plurality of individual flanges (16).

5. The well insert (10) according to claim 4, wherein the permeable membrane (1) is recessed with respect to an end face of the membrane support (10*a*).

6. The well insert (10) according to claim 1, wherein a face of the permeable membrane (1) is flush with respect to an end face of the membrane support (10*a*).

7. The well insert (10) according to claim 1, wherein a peripheral sidewall of the permeable membrane (1) is in contact with a corresponding cylindrical wall of the lower end of the membrane support (10*a*).

8. A method of manufacturing a well insert (10) according to claim 1, comprising the following steps:
    providing the permeable membrane (1);
    providing a source of molten polymer comprising polyolefin material at a temperature T;
    providing an injection moulding tool comprising a male part (3) and a female part (40);
    positioning the permeable membrane (1) in the injection moulding tool;
    closing the injection moulding tool so as to form a cavity in which the permeable membrane (1) is situated, the cavity being shaped so as to conform to the shape of the well insert (10) before solidification of the molten polymer;

injecting a quantity of molten polymer into the cavity, the molten polymer flowing around the periphery of the permeable membrane (1) and intimately contacting the periphery of the permeable membrane (1);

hardening the molten polymer such that it applies a radial force around the periphery of the permeable membrane (1) the polymer exhibiting a linear shrinkage of 1-4% in the radial direction of the permeable membrane (1);

opening the injection moulding tool; and removing the well insert (10) from the injection moulding tool.

9. The method according to claim 8, wherein the polymer exhibits a linear shrinkage of 1.5-2.5% in the radial direction of the permeable membrane (1).

10. The method according to claim 8, wherein the permeable membrane (1) is positioned in the injection moulding tool by means of a vacuum.

11. The method according to claim 10, wherein the male part of the injection moulding tool comprises a seat (35) shaped to receive a permeable membrane (1).

12. The method according to claim 11, wherein the male part (30) of the injection moulding tool further comprises at least three abutments (34) distributed around said seat (35), said abutments being adapted to position the permeable membrane (1) radially.

13. The method according to claim 8, wherein the abutments (34) have a height of at least 0.75 mm and no more than 20% of the thickness of the permeable membrane (1).

14. The method according to claim 11, wherein the male part (30) of the injection moulding tool further comprises at least one abutment (34) shaped so as to fit into a hollow surface feature (1*b*) of the permeable membrane (1).

15. The method according to claim 12, wherein said abutments (34) are provided on a removable insert (45).

16. The method according to claim 8, wherein the female part (40) of the injection moulding tool comprises a vent (42) to permit escape of air during injection of the polymer material, said vent (42) being axial with respect to the permeable membrane (1).

17. The method according to claim 8, wherein, when the injection moulding tool is closed, a play (38) of 2-4 μm is present between a flat surface of the permeable membrane (1) and a surface of the female part of the injection moulding tool which faces said flat surface.

* * * * *